(12) United States Patent
Cater et al.

(10) Patent No.: US 8,109,414 B2
(45) Date of Patent: Feb. 7, 2012

(54) DISCHARGE DEVICE

(75) Inventors: Miro Cater, Daytona Beach, FL (US); Joachim Koerner, Uhldingen-Muehlhofen (DE); Volker Umbeer, Radolfzell (DE); Karl-Heinz Fuchs, Radolfzell (DE)

(73) Assignee: Ing. Erich Pfeiffer GmbH, Radolfzell (DE)

( * ) Notice: Subject to any disclaimer, the term of this patent is extended or adjusted under 35 U.S.C. 154(b) by 680 days.

(21) Appl. No.: 12/287,269

(22) Filed: Oct. 7, 2008

(65) Prior Publication Data

US 2010/0084433 A1    Apr. 8, 2010

(51) Int. Cl.
*B67B 1/00* (2006.01)

(52) U.S. Cl. ............... 222/153.13; 222/63; 222/183; 222/321.7; 222/321.9

(58) Field of Classification Search ........... 222/153.01, 222/153.14, 183, 321.1, 321.7, 321.9, 336, 222/153.13, 63
See application file for complete search history.

(56) References Cited

U.S. PATENT DOCUMENTS

| | | | |
|---|---|---|---|
| 4,674,652 A | 6/1987 | Aten et al. | |
| 4,871,092 A | 10/1989 | Maerte | |
| 4,934,568 A * | 6/1990 | Fuchs | 222/153.13 |
| 5,335,823 A * | 8/1994 | Fuchs et al. | 222/36 |
| 5,878,916 A | 3/1999 | DeJonge | |
| 6,062,433 A * | 5/2000 | Fuchs | 222/153.13 |
| 6,234,366 B1 | 5/2001 | Fuchs | |
| 6,257,454 B1 * | 7/2001 | Ritsche | 222/153.13 |
| 6,427,684 B2 * | 8/2002 | Ritsche et al. | 128/200.23 |
| 6,454,185 B2 | 9/2002 | Fuchs | |
| 2001/0015387 A1 | 8/2001 | Fuchs | |
| 2006/0021614 A1 | 2/2006 | Wermeling et al. | |
| 2009/0120962 A1 | 5/2009 | Malorni et al. | |

FOREIGN PATENT DOCUMENTS

| | | |
|---|---|---|
| CA | 2 497 680 A1 | 3/2004 |
| DE | 40 27 391 A1 | 3/1992 |
| DE | 41 33 274 A1 | 2/1993 |
| DE | 198 07 921 A1 | 8/1999 |
| DE | 102007023012 A1 | 11/2008 |
| EP | 0 472 985 A2 | 3/1992 |
| EP | 1 125 637 A2 | 8/2001 |
| WO | WO 2004/022244 A1 | 3/2004 |
| WO | WO 2006/095194 A1 | 9/2006 |
| WO | WO 2007/095184 A2 | 8/2007 |

OTHER PUBLICATIONS

Office Action from German Patent Office dated Jul. 28, 2009 (4 pages).
European Patent Office Search Report dated Feb. 22, 2010 (11 pages).
European Search Report issued in EP 11166795.2 dated Jun. 24, 2011 (6 pages).
European Search Report issued in EP 11166779.6 dated Jul. 13, 2011 (7 pages).

* cited by examiner

*Primary Examiner* — Frederick C. Nicolas
(74) *Attorney, Agent, or Firm* — Flynn, Thiel, Boutell & Tanis, P.C.

(57) ABSTRACT

A discharge device for media has a housing (10), an operating member (88) manually movable relative to the housing (10) and which, for performing a discharge can be transferred from an unoperated starting position in the direction of an operating direction (1*a*) into an operated end position and with a locking member (52), which is displaceable relative to the housing (10) between a locked position where it prevents the displacement of the operating member (88) into the end position and a release position in which it permits the displacement of the operating member (88) into the end position.

19 Claims, 12 Drawing Sheets

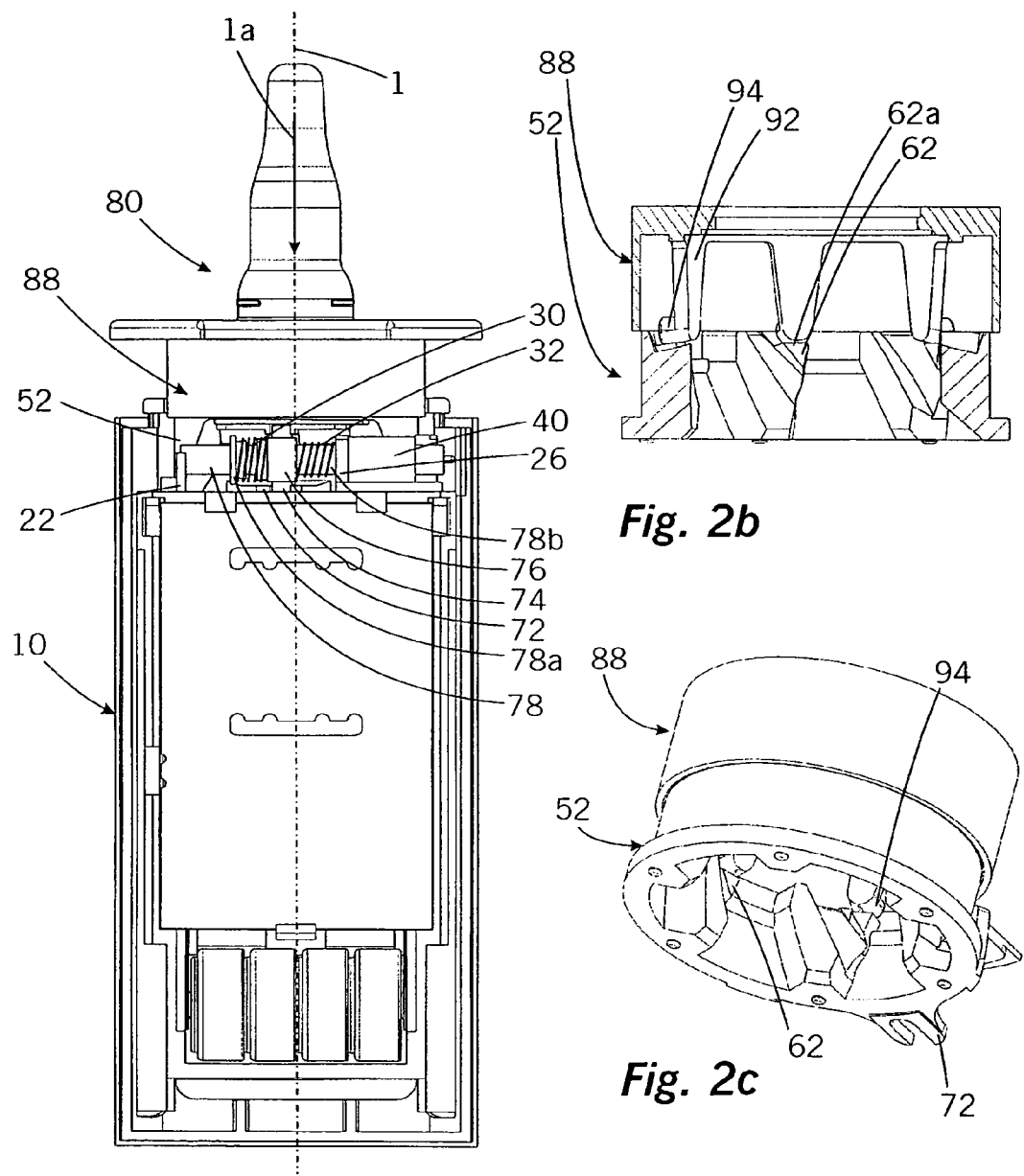

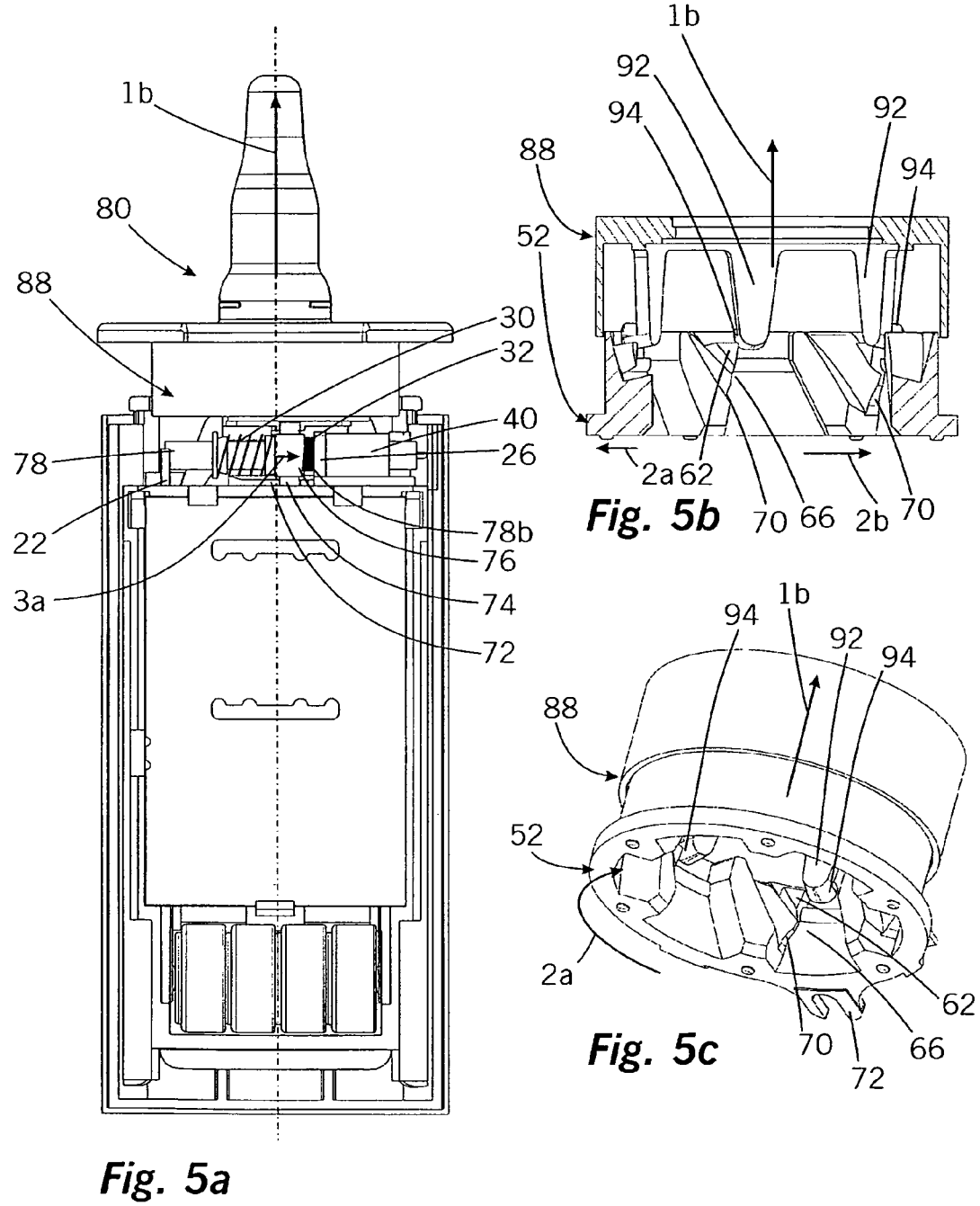

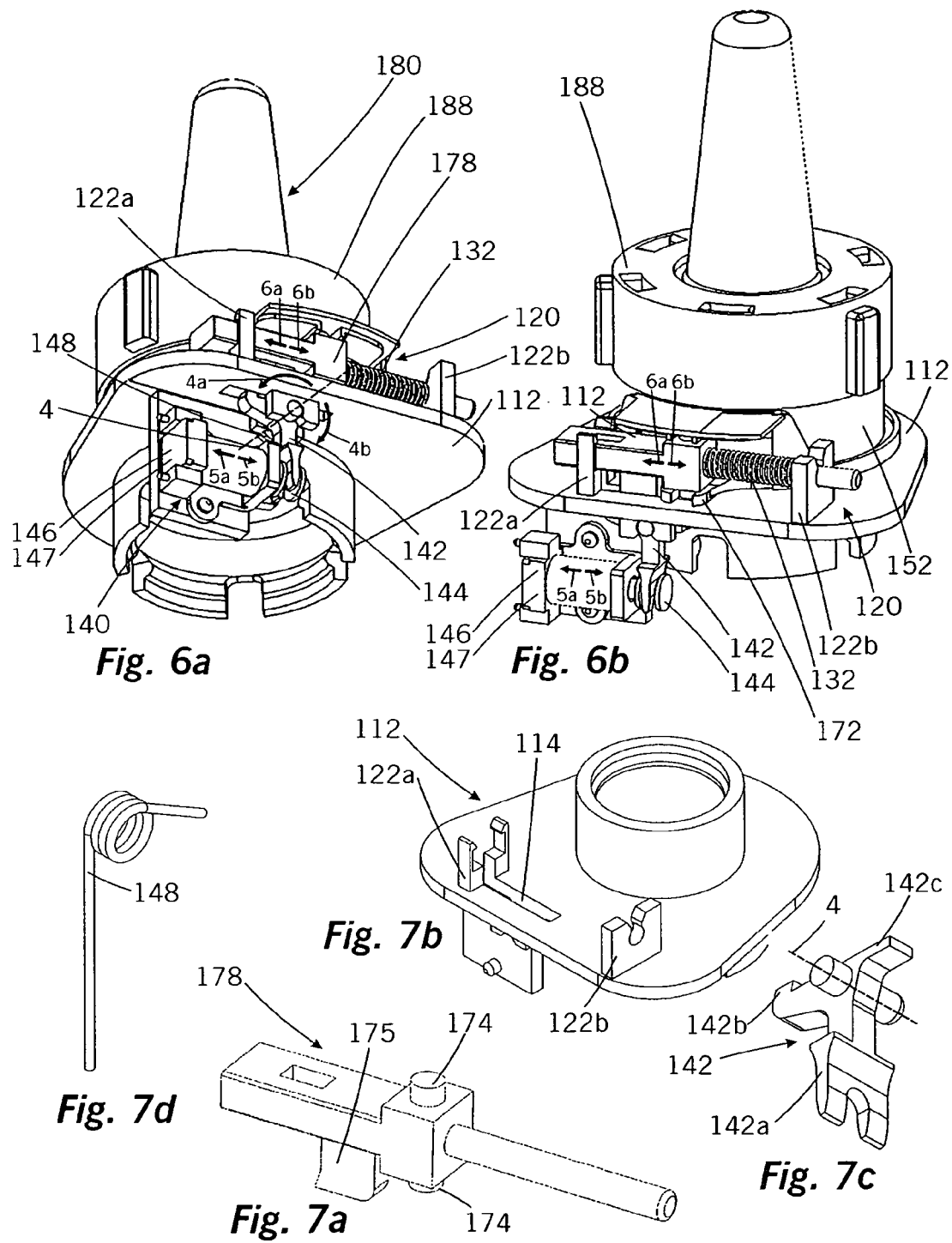

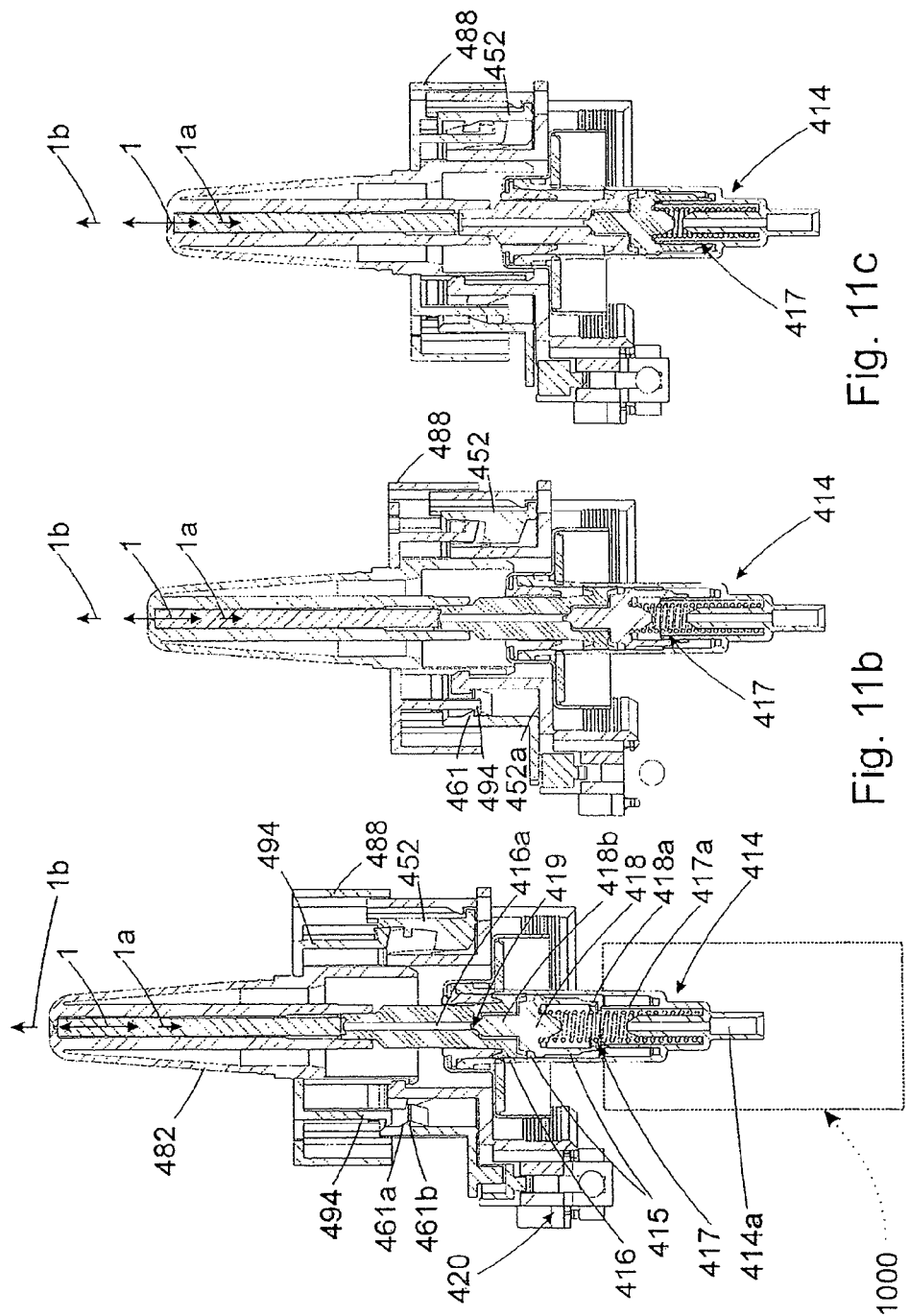

DISCHARGE DEVICE

FIELD OF APPLICATION AND PRIOR ART

The invention relates to a discharge device for media having a housing, an operating member manually movable relative to the housing and which for the operation of a discharge means can be transferred from an unoperated starting position in the operating direction into an operated end position, and a locking member, which is displaceable relative to the housing between a locked position in which it prevents the displacement of the operating member into the end position and a release position in which it allows the displacement of the operating member into the end position.

Such discharge devices are known from the prior part. They are used for the discharge of in particular pharmaceutical media, such as e.g. liquid medicaments. Such discharge devices have a housing in which is provided a discharge means, e.g. a piston pump, which in reaction to a manual movement of the operating member delivers the medium from a medium reservoir to a discharge opening of the discharge device, so that the medium can be delivered to the environment. For operating purposes normally a finger support is provided, which in the prescribed manner is depressed manually by a user relative to the housing in order to trigger the discharge process.

In particular in the case of media which, as a function of the use and dosage, can also have a harmful action, it is advisable for the possibility of a discharge not to be left solely to the judgement of the operator. Therefore such discharge devices have a displaceable locking member, which can prevent a discharge process by mechanically blocking an operation of the operating member. Said locking member can be displaced into its release position as a function of a number of factors, e.g. reacting to an authentication of the user by means of a number code or a fingerprint or in reaction to the end of a predetermined time interval between two discharge processes.

Such a discharge device is e.g. known from EP 1125637 A2, where in the vicinity of the underbody is provided the locking member, which can be moved backwards and forwards between the release position and the locked position by an electromagnet.

Such a discharge device is also disclosed by WO 2007/095184 A1. In the latter a locking member is provided and can be radially displaced under an operating handle and the displacement thereof into the locked position takes place by a spring tension, whereas the transfer into the release position is implemented by an electric motor.

The prior art discharge devices suffer from a number of difficulties and disadvantages. These are the restoring or maintaining of the locked position in the case of a power supply failure, the problem of the high energy requirements in general terms and the prevention of operation in the case of an unusual operating direction and the prior art has still not been able to completely solve these problems.

PROBLEM AND SOLUTION

The problem of the invention is to bring about an improvement compared with the disadvantages of the prior art.

According to the invention this is achieved in that a first spring means is provided applying a force to the locking member in the direction of its release position and the operating member and locking member are so operatively coupled together that in the release position a stroke movement of the operating member from the unoperated starting position into the operated end position and/or a subsequent return stroke movement from the operated end position into the starting position by means of a transmission mechanism leads to energy being fed into the first spring means.

As a result of the inventive solution energy for transferring the locking member into the locked position and also into the release position can be supplied from the energy applied by the user through the operation. Thus, the energy for release in the locked state is stored in the first spring means. As soon as this energy is released the locking member moves into its release position. The return transfer of the locking member is at least sectorwise supplied by the energy introduced into the system by the user on operation. Preferably the movement of the operating member brings about a continuous displacement of the locking member to the locked position or beyond the same counter to the force of the first spring means and consequently on simultaneous tensioning of the first spring means. The term continuous displacement is understood to mean a displacement in which a progressive movement of the operating member preferably in a proportional amount brings about a simultaneous displacement of the locking member.

This type of operative or work coupling makes it possible to force the locking member through the force applied by the user in the direction of its locked position, so that without a corresponding motor and without a spring force application in the direction of the locked position the locked position is restored solely through the operator. The movement of the operating member preferably takes place linearly, especially vertically, relative to a prescribed orientation of the discharge device. The movement direction of the locking member is preferably oriented approximately orthogonally to the movement direction of the operating member, the operative coupling being implementable by corresponding sliding bevels or lever arrangements.

Besides a direct, continuous displacement of the locking member during operation, the feeding of energy into the first spring means can also take place indirectly, e.g. using a further energy storage device, which can e.g. also be constructed as a spring means.

It is particularly advantageous if use can be made of both the stroke movement and the return stroke movement of the operating member by means of a suitable operative coupling in order to bring about the displacement of the locking member. Both during the stroke movement and during the return stroke movement energy is fed into the first spring means. Through this use of both movements of the operating member relative to the housing, an advantageous transmission can be obtained, so that the tensioning of the spring means taking place simultaneously with the movement of the operating member requires no significantly increased operating force on the part of the user.

Spring means in the sense of the invention means any component which can bring about a force application by mechanically stored energy. It is preferably a component in which the energy is stored by elastic deformation, particularly a metallic or plastic helical spring.

The locking member movement brought about the operating member movement need not move the locking member completely into the locked position. Further mechanisms can be provided forcing the locking member towards its locked position over part of the distance.

The operating member can be constructed integrally with a section, which in prescribed manner is operated by an operator during a discharge process. However, preferably the operating member is constructed as a separate component and is connected to the operating handle for joint mobility purposes.

The discharge means is so constructed that at least indirectly a discharge process can be brought about by pressing down the operating member. Preferably the discharge means is a positive displacement pump mechanically coupled to the operating handle. In the locked state of the discharge device, where the locking member is in the locked position, the freedom of movement of the operating handle or the operating member connected thereto is adequately restricted in order to completely or approximately completely prevent an operation of the discharge means.

It is particularly preferred for the operating member and the locking member to be so operatively coupled together that as a result of the movement of the operating member the displacement of the locking member temporarily takes place beyond the locked position. With such a construction the distance covered by the locking member as a result of the stroke movement and/or return stroke movement of the operating member counter to the spring tension of the first spring means is greater than the distance covered by the locking member between the locked position and the release position. Thus, during its movement into its locked position the locking member is initially moved beyond said locked position in conjunction with an excess stroke and is then pressed back into the locked position, e.g. as a result of the action of the first spring means. Such a construction can be advantageous in order to allow the locking sections on the locking member and on the operating member and which in the locked position jointly bring about the locking action to move past one another, so that the locked position can be reliably reachieved following a discharge process.

The operative coupling of the operating member with the locking member is preferably achieved using a connecting link guide by means of which the stroke movement and/or return stroke movement of the operating member causes the displacement of the locking member.

A connecting link guide is understood to mean any mechanism where sections provided in fixed manner on both the locking member and operating member slide on one another whilst the operating member and locking member move in different mutual directions. The movement direction of the operating member and locking member preferably form an angle of 90ø. Preferably the connecting link guide has a connecting link groove on the locking member which cooperates with a cam of the operating member provided for engagement purposes. However, the reverse constellation is also implementable.

In particularly preferred manner the connecting link guide is so constructed that it has a first connecting link groove section into which the cam is introduced during the stroke movement and/or has a second connecting link groove section into which the cam is introduced towards the end of the stroke movement or on passing into the return stroke movement.

It is adequate if one of the two indicated groove sections is provided and in each case the connecting link guide must be so constructed that at the end of the stroke movement the cam describes a structed that at the end of the stroke movement the cam describes a different movement path relative to the locking member during the subsequent return stroke movement. The connecting link groove sections can be constructed as a slot with bilateral contact faces. However, it is sufficient if the connecting link groove sections only have a contact face on one side and against which the cam is pressed as a result of the force of the spring means. In the case of a construction with two connecting link groove sections they are preferably inclined in the opposite direction to the operating direction of the operating member, so that the stroke movement and return stroke movement of the operating member give rise to an equidirectional locking member displacement.

Preferably corresponding control means are provided to ensure that, relative to the locking member, the return stroke movement of the cam takes place on a movement path differing from that of the stroke movement. This can be achieved in that during the stroke movement of the operating member the cam is elastically deflected transversely to the operating direction, a step being provided on the locking member and which during the stroke movement of the operating member and whilst simultaneously reducing the elastic deflection of the cam is overtravelled by the latter. The step can only be overtravelled by the cam during the stroke movement, but not during the opposing return stroke movement, so that following the overtravelling of the cam during the stroke movement the cam movement path during the return stroke differs from the movement path during the stroke, relative to the locking member. Preferably the step is located in the vicinity of the reversal point, i.e. in the vicinity of the last 40%, particularly the last 25% of the stroke path. The elastic deflection of the cam preferably takes place radially and preferably by means of a ramp face, whose face forms with the operating direction of the operating member an acute angle of less than 30ø. The elastic deflection preferably takes place directly through an elastic deformation of the cam or a web on which said cam is provided. However, it is alternatively possible to provide separate spring means, such as e.g. a metal spring.

The step preferably constitutes the transition point between two connecting link groove sections, which are inclined in opposite directions relative to the operating direction so as together bring about a unidirectional movement of the locking member as a result of the stroke and return stroke movements of the operating member. However, constructions are also possible with only a single connecting link groove section in the above-described manner, where the stroke movement of the operating member brings about no locking member movement and only the second connecting link groove section after overtravelling the step or some other reversal by the control means together with the cam leads to the movement of the locking member during the return stroke movement. It is alternatively possible for only the stroke movement by a first groove section to bring about a locking member displacement, whereas at the end of said first groove the step is provided and when the cam has overtravelled the latter the operative coupling between locking member and operating member is eliminated.

In the locked state a stroke movement of the operating member is preferably at least sectorwise prevented in that at least one locking member-side locking section blocks the stroke movement path of at least one operating member-side locking section and it is particularly preferable for the operating member-side locking section to be identical with the cam of the connecting link guide. Thus, with such a construction the cam on the operating member has a double function. In the locked position of the locking member it forms the locking section, which prevents a displacement of the operating member and therefore a discharge. In the release position the cam forms the operating member-side part of the connecting link guide.

The invention is also implemented by such a discharge device, particularly as a further development of the above-described discharge device, where a control arrangement is provided so as to block the movement of the locking member relative to the housing in a blocking state and by a triggering action attainable by means of an electric signal permits the displacement of the locking member from the locked position into the release position.

Thus, such a control arrangement makes it possible to maintain the locking member in the locked position until the electric signal, which can e.g. serve to briefly energize an actuator, cancels out this blocking state. With the above-described construction with a first spring means, which applies a force to the locking member at least indirectly in the direction of the release position, the triggering action leads to the bringing about of the release state.

The electric signal is preferably not intended to make available the energy required for transferring the locking member into the release position and instead permits the release of previously stored mechanical energy for this purpose.

It is particularly preferable for the control arrangement to be constructed in such a way that it is automatically transferred into the blocking state during a displacement of the locking member into the locked position.

In this context an automatic transfer into the blocking state means that without intervention of electronics and in particular through an exclusively mechanically acting mechanism the displacement of the locking member into the locked position gives rise to the blocking state. This can e.g. be achieved in that a detent means acting in the locked position engages with the locking member. It is also possible to have constructions where the blocking is achieved via magnetic or adhesive forces between the housing and the locking member or a locking auxiliary member connected to the locking member.

As a result of this further development a very simple construction is obtained, because it is not necessary to sense the movement of the locking member into the locked position in order in planned manner by means of the discharge device electronics to bring about the blocking state.

In a particularly preferred further development of the invention a bolt member is provided, which in the blocking state of the control arrangement mechanically blocks a displacement of the locking member or a locking auxiliary member operatively connected to the locking member. In conjunction with this invention a locking auxiliary member is understood to be a component so connected to the locking member that during a displacement of the locking member from the release position into the locked position it is displaced in a first direction and during a displacement of the locking member from its locked position into the release position it is displaced in another direction differing therefrom. The locking auxiliary member can be so forcibly coupled that there is a clear association between each position of the locking member and a corresponding position of the locking auxiliary member. However, the locking member and locking auxiliary member can also be interconnected in damped manner, e.g. by a spring arrangement, so that despite the fundamental operative coupling a limited mobility of the locking auxiliary member exists even when the locking member is not moving. A particular advantage of using a locking auxiliary member is that the mobility of the locking auxiliary member can be different from the mobility of the locking member. Thus, in particular there can be a rotary mobility of the locking member, the locking member being operatively coupled to the locking auxiliary member, which is itself only movable in a purely translatory manner.

The above-described further development with a bolt member makes it possible to particularly reliable secure the blocking state and an easy bringing about of the triggering action. Bolt member is understood to mean a component, which can be mechanically engaged with the locking member or locking auxiliary member in order preferably by positive engagement to prevent the movement of the locking member or locking auxiliary member. A spring means can apply a force to the locking member in the direction of the blocking engagement position or counter to said engagement position. For bringing about the blocking state the bolt member is preferably so positioned and/or constructed that it is brought into its engagement state by transferring the locking member into its locked position. This can e.g. be achieved in that the locking member or locking auxiliary member engages an extension on the bolt member on transfer into the locked position and which displaces, more particularly pivots in its entirety said bolt member. It is also possible to have a spring force actuation of the bolt member in the direction of the blocking state. The bolt member can move in translatory manner. However, it is considered particularly advantageous for the bolt member to be mounted in rotary manner on the housing.

In a further development of the invention, in the blocking state of the control arrangement, the locking member or a locking auxiliary member back-connected to the locking member can be held in position by a permanent magnet and as a result thereof the locking member is placed in its locked position. Alternatively the bolt member or a bolt auxiliary member operatively connected to the bolt member is kept by a permanent magnet in a position which leads to the mechanical blocking of the locking member by the bolt member. In these two further developments in each case a permanent magnet is provided for bringing about the blocking state of the control arrangement. In the case of a control arrangement without bolt member either the locking member itself or a locking auxiliary member is force actuated by a permanent magnet on reaching the locked position of the locking member in such a way that the locking member or locking auxiliary member is fixed relative to the housing. In a construction with a bolt member it can be said bolt member or a bolt auxiliary member operatively connected thereto which in the position where it prevents the transfer of the locking member into the release position is fixed by the permanent magnet relative to the housing.

A permanent magnet in this connection is understood to be both a permanent magnetized component and also a conductor through which a current permanently flows and consequently produces a magnetic field. Preferably both on the corresponding movable member and on the locking member, the locking auxiliary member, the bolt member or the bolt auxiliary member, as well as on the housing a permanent magnet is provided in each case. However, it can also be sufficient to have only a single permanent magnet and to have a magnetizable component in place of the second permanent magnet. The particularly advantageous action of the permanent magnet in conjunction with this invention is that the force applied by the permanent magnet which acts on the locking member, locking auxiliary member, bolt member or bolt auxiliary member very rapidly decreases if the corresponding member is removed from the casing-fixed permanent magnet, so that the action of the permanent magnet relates in isolated manner to the locked state, but very soon becomes negligible on transfer into the release state.

In the case of a construction with a permanent magnet which is directly or indirectly responsible for keeping the locking member in its locked position, it is particularly preferable if the force exerted by the permanent magnet or magnets in an end position which is associated with the locked position of the locking member is higher than the force from spring means of the discharge device in the locked position of the locking member acting in the opposite direction on the locking member, locking auxiliary member, bolt member or bolt auxiliary member. With such a construction if the locking member is in the locked state a blocking action can be achieved through the spring tension, which directly or indirectly forces the locking member in the direction of the release position or the bolt member in the direction of an unlocked state, is lower than the force brought about in this position by the permanent magnet. Thus, such a high force is applied by the permanent magnet to the corresponding member that the spring tensions acting in the opposite direction cannot lead to a movement of the locking member into the release position or the bolt member into its unlocked position. Only when the corresponding member by an additional force actuation has been moved sufficiently far from the action area of the permanent magnet does the spring tension preponderate and consequently directly or indirectly leads to a transfer of the locking member into its release position.

In a further development of the invention, in order to bring about a triggering action an electrically controllable actuator is provided, preferably an electromagnet, through which a force can be applied either to the locking member or a locking auxiliary member operatively connected to the locking member, so that as a result the locking member is moved towards its release position. Alternatively the electrically controllable actuator can be used for applying a force to the bolt member or the bolt auxiliary member operatively connected to the bolt member, the force actuation taking place in a direction which leads to a cancelling of the mechanical blocking of the locking member by the bolt member and therefore to a displacement of the locking member towards its release position. According to this further development the actuator is provided for bringing about a force actuation of the corresponding member in reaction to an energizing by a control device of the discharge device in order to displace said member towards the release position or in the case of the bolt member towards the disengaged position. The actuator is not used for supplying all the mechanical energy necessary for this purpose and instead merely overcomes the previously prevailing blocking effect, e.g. in that for a short time period, preferably less than 50 ms, a force actuation takes place counter to the force actuation of the previously described permanent magnet. The corresponding member, e.g. the locking auxiliary member or bolt auxiliary member, is released by a brief force application from the permanent magnet and/or is moved sufficiently far out of its action range to enable there to be a subsequent displacement of the bolt member into its disengaged position and/or the locking member into its release position as a result of the force actuation of the first spring means and/or another spring means.

The use of an electromagnet as the actuator is particularly advantageous, because such an electromagnet can be very inexpensive and small. In addition, the control of such an electromagnet by control electronics of the discharge device is very simple, because a mere short energizing is sufficient for bringing about the desired effect.

To achieve the aforementioned objective, it is particularly advantageous if the electrically controllable actuator is constructed for exerting a force on the locking member, locking auxiliary member, bolt member or bolt auxiliary member, which is higher than the force acting in the opposite direction and resulting from the permanent magnet force acting on the corresponding member and preferably the force of a spring means applying force to said member.

Through such a construction, in which the control device brings about a sufficiently high and prescribed energizing of the actuator, a corresponding movement of the member counter to the force of the permanent magnet can be obtained until the resulting force acting on the member in the direction of the disengaged or release position is higher than the permanent magnet force acting in the opposite direction.

The invention is also implemented by such a discharge device in which the locking member is constructed to rotate about a rotation axis oriented in the operating direction for the transfer from the locked position into the release position and has distributed over its circumference at least three locking sections, which are so placed in the locked position of the locking member that a stroke movement of the operating member is prevented.

Such a construction permits a particularly secure locked position, because independently of whether and in what direction the operating member is depressed transversely to the operating direction of the prescribed use, at least one locking section is always present which prevents a movement of the operating member with the discharge process associated therewith. The rotatability of the locking member makes it possible to implement this particularly secure locked position with a comparatively simple mechanical design, because the rotation of an integral locking ring is sufficient to simultaneously displace all three or more locking sections into the locked position. It is considered particularly preferable for there to be at least six locking sections on the locking member and/or for the locking sections to be uniformly distributed over the circular path.

The rotatability of the locking member about the rotation axis can be limited with regards to the rotation angle, so that a transfer from the locked position into the release position and from the release position into the locked position can be carried out in mutually opposing directions. However, alternatively and in the manner known in connection with ball point pens, it is also possible not to limit the rotatability of the locking member and instead allow a complete rotation about its rotation axis of said locking member, so that the transfer into the locked position and the transfer into the release position always takes place in the same rotation direction and on sides of the operating member and locking member with each release and locking cycle other locking sections on the locking member and on the operating member come into contact with one another until the locking member and operating member have performed a complete 360ø rotation relative to one another.

It is particularly preferable for the locking member to surround in all-round manner the operating member and for the rotation axis of the locking member to be parallel to the operating direction and preferably coaxial to a centre axis of the discharge device. This permits particularly compact constructions. With such a design the locking member is roughly annular and has a central recess through which the operating member or operating handle is connected to the discharge means of the discharge device.

Preferably the locking member-side locking sections point radially inwards from an inner face of the locking member and the corresponding operating member-side locking sections point radially outwards. Such a construction is advantageous, because a circumferential surface of the locking member on whose inside are provided the locking sections constitutes a protection against manually influencing by an operator. The locking sections which prevent operation in the locked position are difficultly accessible and therefore well protected by the circumferential surface.

In a further development of the invention a piezoelectric or electric motor is provided for moving the locking member, locking auxiliary member, bolt member or bolt auxiliary member. Such a piezoelectric motor is very light and has a high power compared with its construction volume. The piezoelectric motor is preferably casing-fixed and engages via an actuator on the corresponding member. The operative coupling between actuator and locking member is preferably such that the locking member is movable relative to the piezoelectric motor counter to a holding or retaining force, e.g. a frictional force, because it makes it possible to only use the piezoelectric motor e.g. for bringing about the release position, whereas the locked position is brought about indirectly in the above-described manner via the operating handle and its operative coupling to the locking member. It is particularly advantageous for the coupling between the actuator of the piezoelectric motor and the locking member to be solely by frictional engagement.

In a further development the electric or piezoelectric motor is provided for the movement of a cam member, preferably for the rotary movement of a cam disk, the cam member being constructed for directly preventing the movement of the locking member or a locking auxiliary member into the locked position of the locking member or indirectly via a bolt member the movement of the locking member or a locking auxiliary member into the locked position of the locking member and preferably a spring force acts on the bolt member in the direction of its release or disengagement position and through the cam member and as a function of its position is held in the blocking position.

Furthermore, the invention is related to a discharge device of that kind, in particular a discharge device according to the above described configuration in which a return lock is provided and which after reaching a defined intermediate locking position during a transition of the operating member from the starting position of the end position, prevent a return of the operating member to the starting position as long as said operating member will be transferred to the end position.

Such a return lock effects that after start of an operation and the thereby resulting trespassing of the intermediate locking position, an immediate return movement of the operating member into the starting position is prevented. Such a return is not allowed until the operating member has previously been transferred up to the end position. In the context of this advanced embodiment an end position is to mean a position of the operating member which after release of the operating member brings about said locking position. In the case of an embodiment having two connecting link groove sections, the end position is e.g. reached as soon as the cam is engaged in the second connecting link groove section.

Said configuration prevents any malpractice by a user who tries to discharge an improperly high liquid amount and merely executes a partial stroke initiating from the starting position with the intention to prevent the locking member from moving into the locking position due to performance of a complete stroke. The return lock compels that after a started stroke movement of the operating member, said member is meanwhile also transferred up to the stroke end position to allow the start of a subsequent new stroke. Thus, after the start of a stroke movement, the starting position is achievable only together with the locking position.

A particular embodiment of the return lock is arranged to inhibit any return stroke movement unless the end position is reached. To that effect, e.g. a ladder-type detent device may be provided which up to reaching the end position always ensures a progressive stroke movement, and thus also prevents partial return strokes. A simplified configuration is arranged to allow action of the return lock merely in a defined intermediate locking position so that after a stroke movement exceeding the intermediate locking position, any return stroke is possible but to said intermediate locking position.

In an advanced embodiment of the invention, the discharge device includes a pump having a volume variable pump chamber, the pump being configured in such a way that a filling of the pump chamber within a return stroke will not occur until a defined intermediate filling position is reached, said intermediate filling position being arranged in such a way that it will be reached only, when the operating member is positioned at a location between the intermediate lock position and the starting position.

Thus, in such a configuration is provided a pump which during a return stroke will not continuously aspirate medium from a medium reservoir, but will e.g. initially produce a vacuum in the pump chamber, while an inlet valve to the pump chamber remains closed. Only upon reaching the intermediate filling position, the inlet valve opens to effect an abrupt injection of medium from the medium reservoir into the pump chamber due to the produced vacuum. The arrangement in which the intermediate filling position may be reached not earlier than the operating member is located between the intermediate locking position and the starting position, has the effect that after the operating member has trespassed the intermediate locking position in the stroke direction, a refilling of the pump chamber is possible only if the operating member has previously been moved up to its end position by completing the stroke movement, as it is the thus allowed subsequent return stroke movement in the direction of the starting position that will enable a return trespassing of the intermediate locking position in the direction of the return stroke. Thus is ensured that the refilling of the pump chamber is mandatorily coupled to the reaching of the locking position. Any improper employment by a user who executes partial stroke movements between the intermediate locking position and the end position of the operating member will thus not succeed in a medium discharge.

In an advanced embodiment, the return lock may include detent means, a first component of the detent means being disposed fixedly relative to the housing and a second component of the detent means, which is constructed for cooperation with the first component, being disposed fixedly relative to the operating member in the operating direction.

Said detent means are arranged in such a way that the second component of the detent means which is disposed fixedly relative to the operating member, is capable of trespassing the first component only in the stroke direction, but not in the return stroke direction. Thus, during a stroke movement the second component of the detent means, e.g. a snap member deflectable in a radial direction, is directed along the first component, e.g. a step, and is thereby intermittently deflected. As soon as said first component of the detent means has been overridden by the second component, any return to the starting position is inhibited without an intermediate reaching of the end position of the operating member. The configuration having detent means is simple to manufacture and particularly cost effective. As said second component of the detent means, cams may be provided which may be identical to the above described cams for engagement of the connecting link groove or may be disposed in an offset position relative to the latter. The first component of the detent means, as e.g. a step, may be disposed in the vicinity of such a connecting link groove or separate from the connecting link groove.

To prevent that the action of the return lock will be avoided by forcibly drawing the operating member from the partial stroke position back to the starting position, a level out device may be provided between the externally accessible surfaces of the discharge device and the second component of the detent means which will undergo telescopic yielding upon such a use of force, and thus prevent a separation of the detent means. Also conceived is that the level out device is provided as a predetermined breaking member which will disrupt upon use of force, and thus permanently prevent further actuating operations.

BRIEF DESCRIPTION OF THE DRAWINGS

Further advantages and features of the invention can be gathered from the claims, the following description of preferred embodiments of the attached drawings, wherein show:

FIGS. 2a to 5c The discharge device of FIGS. 1a to 1f in different stages of use and in detail.

FIGS. 2a to 2c A discharge device in a locked state.

FIGS. 5a to 5c The discharge device following a return stroke movement.

FIGS. 6a to 6b A second embodiment of an inventive discharge device only showing the components essential for the invention.

FIGS. 7a to 7d Individual components of the embodiment of FIG. 6a/6b.

FIGS. 11a to 11c A fifth embodiment of an inventive discharge device showing different stages during operation.

DETAILED DESCRIPTION OF THE EMBODIMENTS

FIGS. 1a to 1f show an inventive discharge device or details thereof in different perspectives.

Figures 1A, 1B:
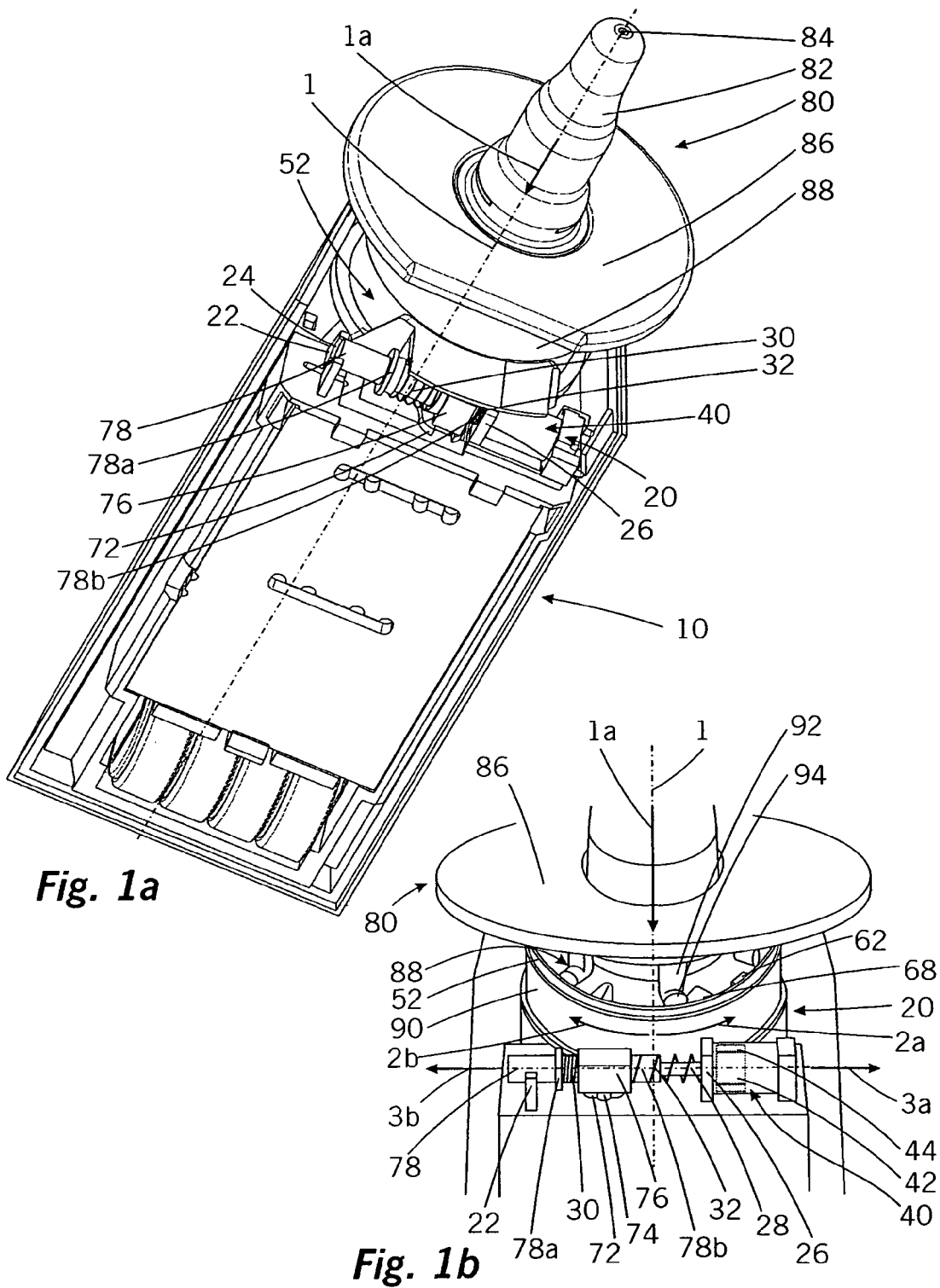
FIGS. 1a to 1f A first embodiment of an inventive discharge device.
Figure 1D:
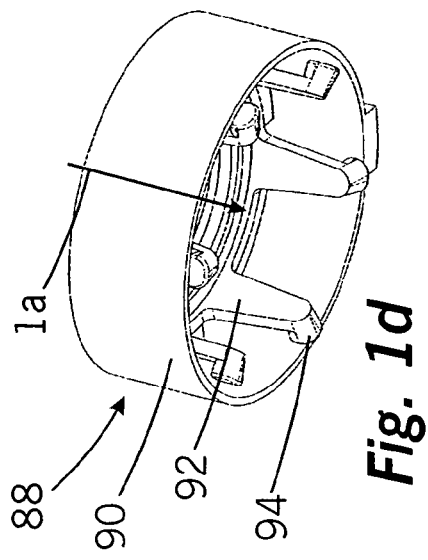

FIG. 1a shows the overall device in a state with the electronic module removed and which in operation is coupled to the front side. FIG. 1b shows the locking mechanism of the discharge device in detail. FIGS. 1c to 1f show sectional, perspective views of an operating member and a locking member of the discharge device, said members representing the core of the locking mechanism.

FIGS. 1a to 1f serve to illustrate the individual elements of the discharge device. The interaction is explained relative to FIGS. 2 to 5.

The discharge device of FIG. 1a has a housing 10 which, in addition to a media reservoir 1000 and a not shown pumping device, has a locking mechanism 20. To the upper end an applicator subassembly 80 comprising several components, but which is rigid, is connected above the locking mechanism 20 to housing 10. Subassembly 80 has in addition to a nose olive 82 with outlet opening 84 an operating handle 86, which is moved in an operating direction 1a relative to housing 10 in translatory manner counter to the spring tension of a not shown pump spring. This displacement of the applicator subassembly leads in not shown manner to an operation of the pump provided in the housing 10 and whose pumping chamber volume is consequently reduced, so that the medium present beforehand in the pumping chamber is discharged through the outlet opening 84.

The special feature of the discharge device is constituted by the locking mechanism 20 which is used to allow or prevent the movement of the applicator subassembly 80 in operating direction 1a as a function of peripheral parameters. To this end the locking mechanism 20 comprises on the applicator subassembly 80 below the operating handle 86 a roughly annular operating member 88, which is separately constructed in FIGS. 1c and 1d and is shown for illustration in FIG. 1b with a part sectional circumferential surface 90.

Within the circumferential surface 90 of operating member 88 a total of six cam carriers 92 extend vertically downwards and on the end of each of these is provided an outwardly pointing cam 94. The six cam carriers 92 with cams 94 are uniformly arranged over an arc and are consequently in each case spaced by 60ø. The operating member 88 and therefore also the cams 94 are connected in fixed manner to operating handle 86 and the other elements of the applicator subassembly 80. Thus, a depression of operating handle 88 always leads to a depression of the cams 94. Whilst applicator subassembly 80 is movable relative to housing 10 in operating direction 1a, there are no further extending degrees of freedom. Thus, the applicator subassembly 80 cannot be rotated about axis 1 of operating direction 1a relative to housing 10 and instead always remains in a clearly defined angular position relative to housing 10.

Figure 1F:
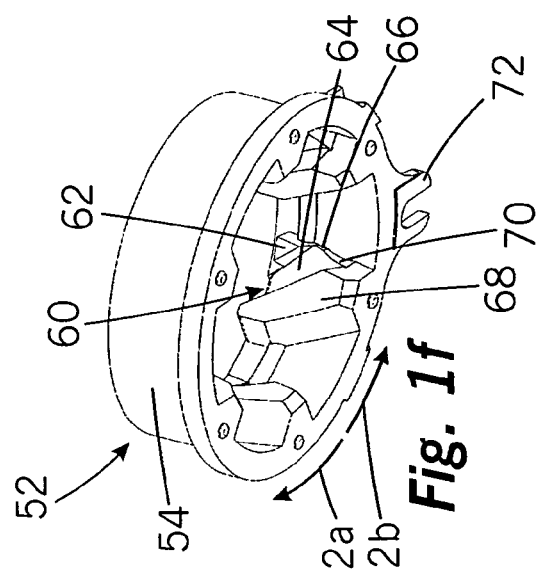
Figure 1C:
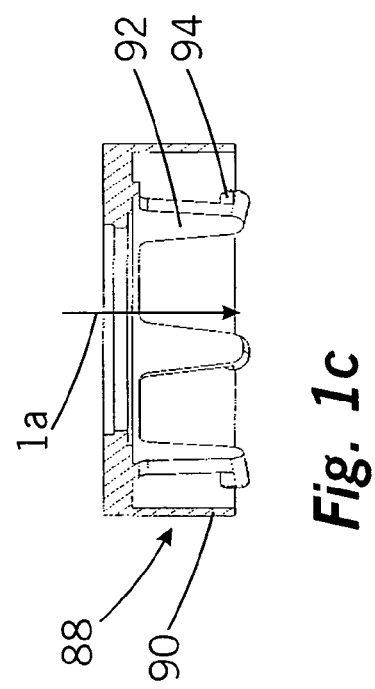
Figure 1E:
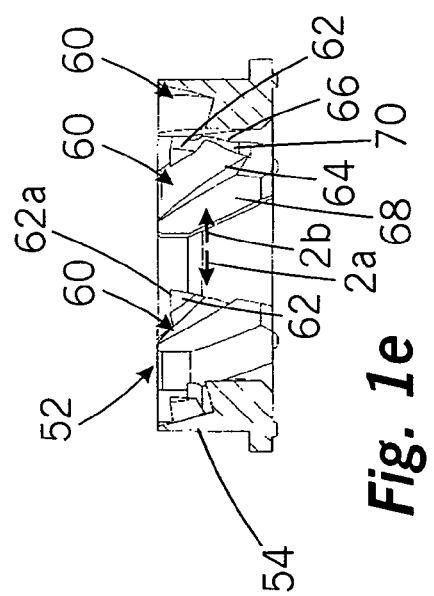

A locking member 52 is provided in corresponding manner to operating member 88 and is shown separately in FIGS. 1e and 1f and can also be seen in the representation of FIG. 1b.

Like the operating member 88, said locking member 52 is approximately annular and is bounded by an outer circumferential surface 54, the external diameter of said circumferential surface 54 being smaller than the internal diameter of circumferential surface 90 of operating member 88, so that the circumferential surfaces 54 and 90 can be telescoped. Unlike the operating member 88, locking member 52 is not movable in operating direction 1a and is instead always at the same height relative to housing 10. However, to a limited extent the locking member 52 can be rotated in direction 2a, 2b about a main axis 1 oriented coaxially to the operating direction 1a. In corresponding manner to the cams 94 on operating member 88, on locking member 52 there are a total of six identically shaped and inwardly pointing functional sections 60, which extend radially inwards from the circumferential surface 54. They are in each case provided on their upper end with a locking section 62 having a roughly planar, upper terminating face 62a. They also have in each case a first connecting link groove section 64 and a second connecting link groove section 66. Whereas the first connecting link groove section is firstly bounded by a locking section 62 and secondly by an elevation 68 and is slightly radially inwardly inclined in direction 1a, the second connecting link groove section 66 is solely formed by the outer edge of functional section 60 on the right relative to FIG. 1e. The transition from the first connecting link groove section 64 into the second connecting link groove section 66 is formed by a step 70 on said right-hand outer edge of functional section 60.

As is clear from FIGS. 1b and 1f, a guide fork 72 extends radially outwards from circumferential surface 54 and guides a pin 74, which is fitted integrally to a sleeve element 76. The sleeve element 76 is mounted in floating manner on a push rod 78. In the sense of the present invention, the sleeve element 76 and in particular the push rod 78 are understood to be locking auxiliary members associated with locking member 52.

Unlike in the case of locking member 52, push rod 78 cannot be rotated about rotation axis 1 and is instead only movable in translatory manner in directions 3a, 3b along a movement axis 3 oriented tangentially to the rotary locking member 52.

The push rod 78 is bilaterally mounted. Firstly on the housing is provided a receptacle 22 with a semicircular recess 24 in which is located the left-hand end of push rod 78 relative to FIG. 1b. Secondly to the right of push rod 78 is provided a stop face 26 from where extends a guide mandrel 28 in direction 3b and on which the push rod 78 is engaged by means of a not shown bore in push rod 78.

To the left of the sleeve 76 mounted in floating manner on push rod 78 a circumferential push rod flange 78a is integrally provided on push rod 78. A push rod spring 30 constructed as a spiral spring is provided between push rod flange 78a and sleeve 26. Between the right-side end of sleeve 76 and stop face 26 is provided a release spring 32. The right-side end 78b of push rod 78 surrounded by release spring 32 is constructed permanent magnetically in not shown manner. For cooperating with said permanent magnetic ends 78b of push rod 78 to the right of the stop face 26 a magnetic unit 40 is provided in casing-fixed manner and has the permanent magnet 42 shown in dotted line form in FIG. 1b and which applies a force in direction 3a to the push rod and also has an electromagnet 44 shown in dotted line form and which is constructed to apply a force to push rod 78 on energizing in the direction of arrow 3b.

The embodiment of an inventive discharge device shown in FIGS. 1a to 1f makes it possible by means of the locking member and operating member to block or allow, as desired, a discharge process in a particularly reliable, energy-efficient manner.

Operation will be explained in greater detail relative to FIGS. 2 to 5.

FIGS. 2a to 2c show a starting state in which a discharge process is blocked. As can be gathered from FIG. 2a, in this state the push rod 78 engages on stop face 26. Despite the spring force or tension of springs 30, 32 which actuate push rod 78 in direction 3b, the push rod 78 is not detached from stop face 26, because the permanent magnets 78b, 42 in magnet unit 40 and on the right-hand end of the push rod 76 bring about a higher force application to the push rod 78 in direction 3a than springs 30, 32 in the opposite direction 3b. The position of the sleeve element 76 consequently results from the equilibrium of forces at springs 30, 32.

As is clear from the previously explained FIG. 1b, the position of sleeve elements 76 via pin 74 and guide fork 72 prescribe the rotary position of locking member 52. FIGS. 2b and 2c show the rotary position relative to cams 94 in the state of FIG. 2a. It is not clear that in this rotary position the cams 94 are in each case placed directly above locking sections 62.

If in the state of FIGS. 2a to 2c there is an operation by the operator, the operating member 88 can only be moved to a very limited extent in direction 1a. The movement of the operating member 88 ends as soon as the cams 94 engage on the top side faces 62a of locking section 62. As the locking member 52 is not movable in direction 1a, a further extending movement of operating member 88 and therefore a discharge of medium is impossible.

As a result of the six cams 94, which are circumferentially distributed, even a non-prescribed, violent force actuation of operating member 88 orthogonally to the operating direction 1a does not lead to a sliding of all the cams 94 from faces 62a of locking section 62. Even if such a sliding off was brought about on one side, this can never be achieved for all the cams 94. Thus, the locked state of the discharge device is completely secure.

The discharge device is constructed so that after a time interval following a prior use predeterminable e.g. by a doctor and stored in the discharge device electronics, the discharge device can again be transferred from its locked position into its release position. The release state and the achieving of the release state will be described hereinafter relative to FIGS. 3a to 3c.

Release is brought about by energizing electromagnet 44 in magnet unit 40. This energization is triggered by a not shown control device, which initiates the transfer into the release state as a function of the indicated peripheral parameters. Energization leads to a force actuation of the right-hand end of push rod 78 in direction 3b. Jointly with the spring tension of springs 30, 32, the resulting force acting on push rod 78 in direction 3b exceeds the force of permanents magnet 7b, 42 acting in the opposite direction 3a. Thus, the push rod 78 is disengaged from the stop face 26 and, supplied with the spring energy of springs 30, 32 moves in direction 3b until the push rod flange 78a strikes against receptacle 22.

The action of permanent magnets 76b, 42 is locally very limited, so that even when there is a small spacing between push rod 78 and stop face 26 said action becomes negligible. During the movement of push rod 78 it is consequently unnecessary to maintain the energizing of the electromagnet 44 of magnet unit 40, because in the case of a corresponding design of permanent magnets 78b, 42 and springs 30,32 a short pulse is sufficient to bring the push rod 78 into the position shown in FIG. 3a.

Figures 3A, 3B, 3C:
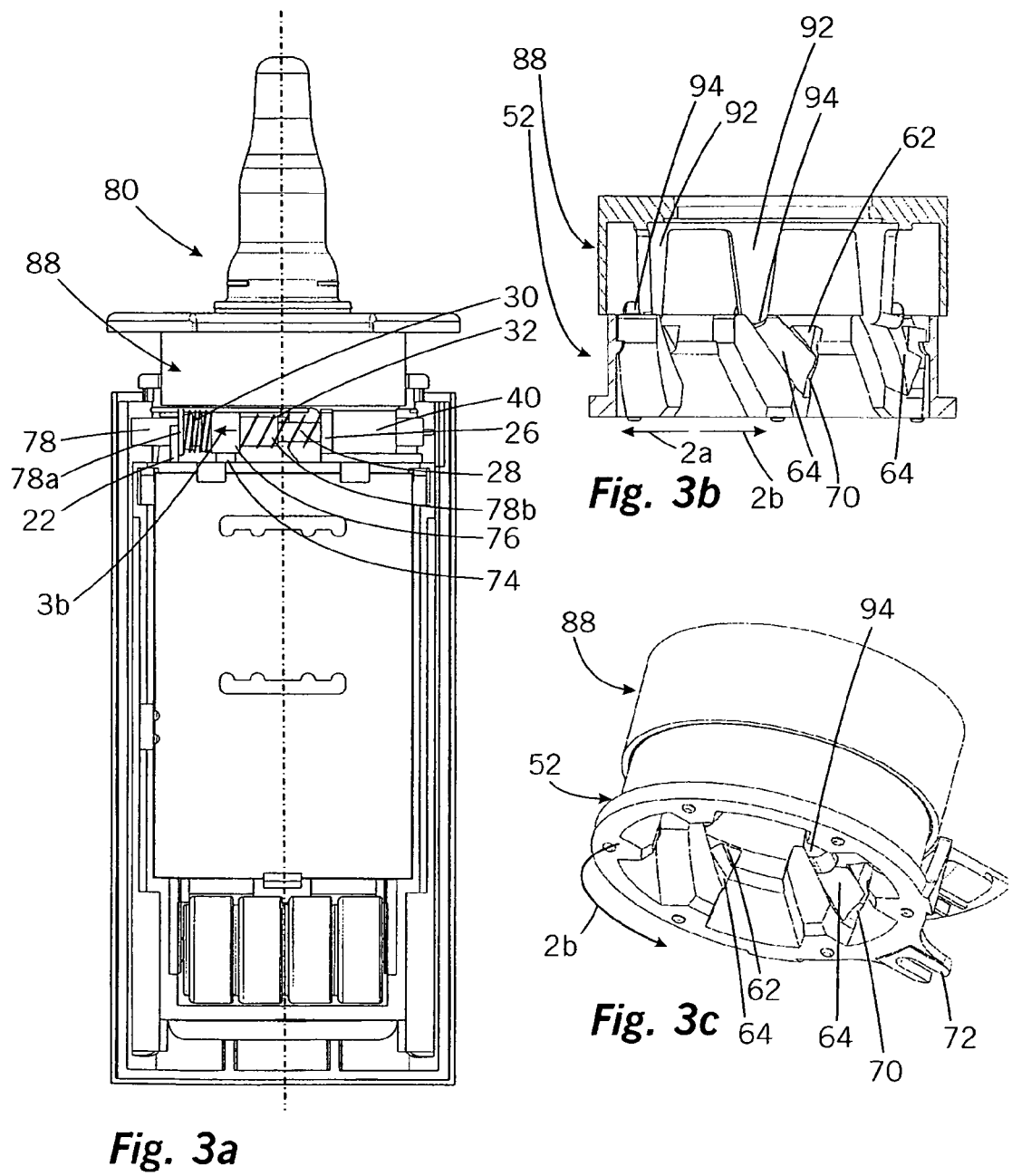
FIGS. 3a to 3c The discharge device in a release state.

In the represented end position of push rod 78, the position of sleeve element 76 is once again such that the force in each case emanating from springs 30 and 32 is identical. As a result of the fact that the right-hand release spring 32 is much harder, sleeve 76 is moved comparatively far in direction 3b. FIGS. 3b and 3c show the resulting relative position of operating member 88 and locking member 52. It is clear that, relative to the perspective of FIG. 3b, the locking member has moved to the right in direction 2b, so that the cams 94 are no longer above the locking sections 62 and are instead above the inlet areas of the first connecting link groove sections 64 and as a result of the inclined position of the latter rotate the locking member 52 to the left in direction 2a relative to the perspective of FIG. 3b. The pressing down of the operating member 88 associated with a discharge process consequently takes place simultaneously with a movement of locking member 52 in the direction of the locked position. The L-shaped design of the cam carriers 92 and cams 94 ensure that the cam carriers 92 do not collide with the locking sections 60 during the movement from the state of FIG. 3a into the state of FIG. 4a.

During the downward movement of operating member 88 in direction 1a, an elastic tension state is produced in the cam carriers 92, because as a result of the shaping of the first groove sections 64 the cams 94 are radially increasingly deflected inwards. As soon as the cams 94 have reached the lower end of the grooves of sections 64, they are shoved over the end-forming step 70, which leads to a sudden release of the tensioned cam carriers 92, so that the cams 94 are once again displaced radially outwards.

Figures 4A, 4B, 4C:
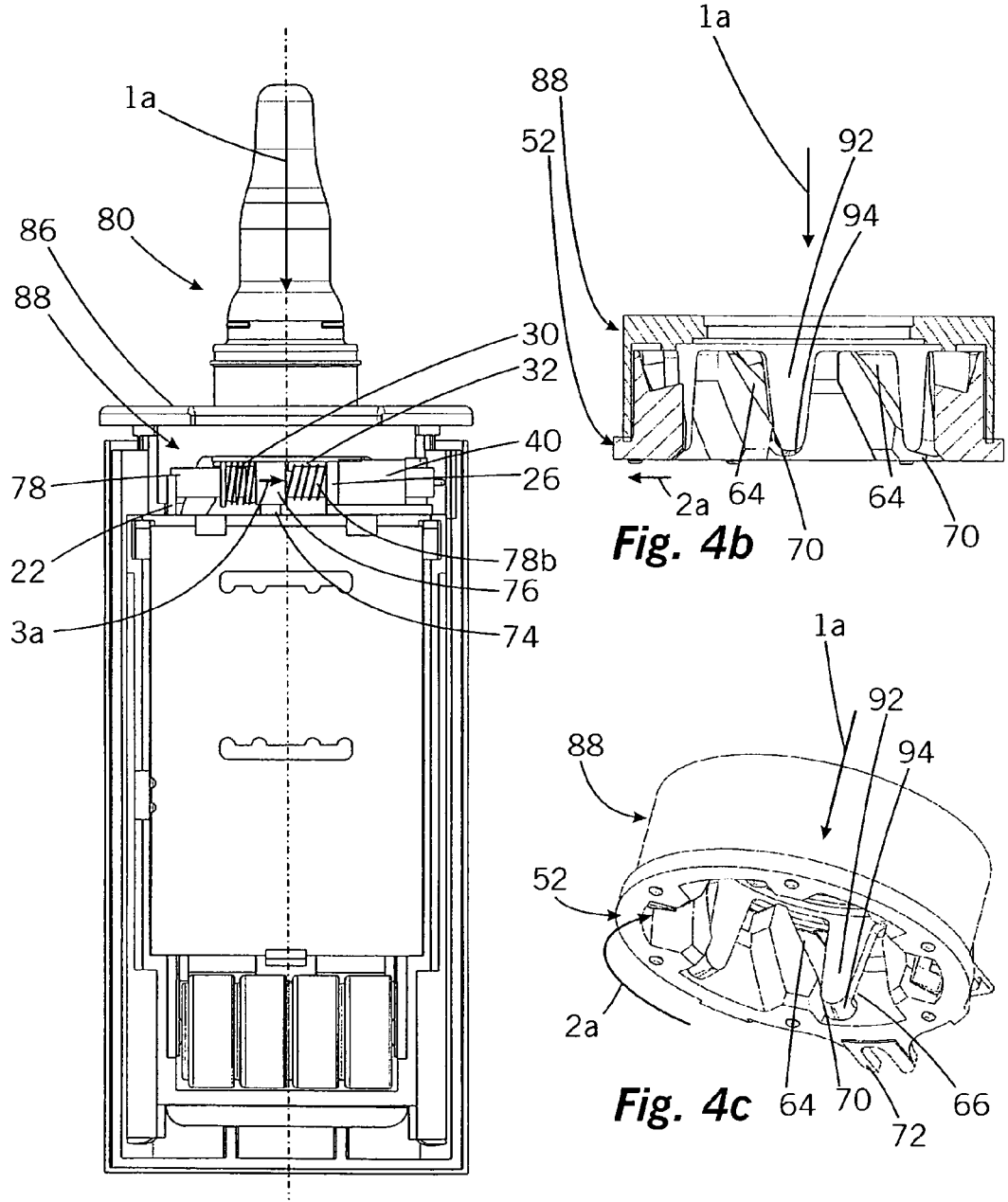
FIGS. 4a to 4c The discharge device following a stroke movement.

FIGS. 4a to 4c show the resulting state, which roughly represents the reversal point between the stroke movement and the return stroke movement, as a result of the rotary movement which has already taken place of the locking member 52, once again the state is reached in which the push rod 78 engages on stop face 26. Thus, in the above-described manner, it is again held in this state by the permanent magnets 78b and 42.

The discharge process is already ended on reaching the state of FIGS. 4a to 4c. Starting from the state of FIGS. 4a to 4c, the return stroke movement takes place as soon as the operator eliminates the force actuation of the operating member 88 downwards in the direction 1a. As soon as this takes place, the entire applicator subassembly 80, together with the operating member 88, is displaced upwards counter to direction 1a by the not shown restoring spring of the pumping device. Through the cams 94 having moved beyond the step 70, it is impossible for there to be an opposing movement path of the cams 94 along the first connecting link groove sections 64. Instead the cams 94 move along the second connecting link groove sections 66, i.e. upwards along the right-side edge of the functional section 60, so that, relative to FIG. 4b, the rotation of the locking member 52 is continued to the left in direction 2a. As a corresponding movement of push rod 78 in direction 3a is no longer possible, because in this phase the push rod 78 already engages against the stop face 26, as a result of this further rotation of locking member 52 in direction 2a there is only a joint displacement of the sleeve element 76. Simultaneously the right-side release spring 32 is further compressed between sleeve element 76 and stop face 26.

FIGS. 5a to 5c show the final phase of the return stroke. As can be seen in FIG. 5a, in the meantime the release spring 32 has reached an extremely compressed state which is reached, as shown in FIGS. 5b and 5c when cams 94 slide along the outer edge of the functional sections in the vicinity of the right-side tip of the locking sections 62.

In the instant when the cams 94 are disengaged from the locking sections 62 and therefore leave the second connecting link groove section 66, the extremely compressed release spring 32 suddenly presses the sleeve inwards, which in the perspective of FIGS. 5b and 5c leads to a rotation to the right of locking member 52 counter to direction 2a. This movement ends as soon as an equilibrium of forces again prevails at springs 30, 32. As a result of the movement the cams 94 are again displaced relative to locking sections 62 so that they assume their locked position above said sections 62, which once again gives the state of FIGS. 2a to 2c.

The described design provides a locking mechanism for a discharge device, in which for the movement of the corresponding locking member there is no need for any energy source in the discharge device, because the transfer into the locked position occurs directly through the energy introduced by the operator and because a triggering means, e.g. in the form of an electromagnet 44 is provided. However, the function of said electromagnet 44 is not to provide the energy necessary for displacing the locking member and instead merely brings about a brief limited additional force application to the push rod, which together with the force of springs 30, 32 leads to the push rod being detached from the stop face 26.

FIGS. 6a and 6b show a second embodiment of an inventive discharge device. With regards to many features and components it coincides with the first embodiment. In particular, the operating member 188 and locking member 152 are almost identical to the previously described embodiment.

Differences more particularly exist relative to the locking mechanism 120. These differences are explained relative to FIGS. 6a and 6b and the individual part representations of FIGS. 7a to 7d.

As can in particular be gathered from FIG. 6b, the rotary mounted locking member 152 also has in this second embodiment radially outwardly directed guide forks 172 by means of which a coupling is implemented between the locking member 154 and the translatory movable parts of locking mechanism 120. Diverging from the embodiment of the preceding drawings, in the second embodiment the guide forks 172 contain as the locking auxiliary member a rigid push rod component 178 and this is shown in detail in FIG. 7a. Said push rod component 178 is inserted by means of two pins 174 in guide forks 172 and is also mounted on the housing side in two bearing bushes 122a, 122b, so that the push rod component 178 can only be moved in translatory manner. On the underside of the push rod component 178 is provided a locking cam 175, which passes through a gap 114 in a plate 112 closing the top of the housing 110 and shown in detail in FIG. 7b, in order to cooperate with the subsequently described, further components of locking mechanism 120. A release spring 132 permanently force-actuates the push rod component 178 to the left in direction 6a, i.e. in the release position direction.

As is apparent from the forcible coupling of the push rod component 178 and locking member 152, by means of the position of said component 178 it is possible to control whether the discharge device is in a release or a locked state. In order to attain the release state the push rod component 178 must be moved into its left-side end position, whereas in its right-hand side end position it prevents an operation of the discharge device.

Below plate 112 is provided a control arrangement 140, which cooperates in prescribed manner with the locking cam 175. Said control arrangement 140 comprises a pivotable bolt 142, which is articulated to housing plate 112 about a rotation axis 4. As shown in FIG. 7c, the bolt 142 has a downwardly pointing operating section 142, an engagement section 142 pointing to the left in FIGS. 6a and 6b and a restoring section 142c pointing to the right. As can in particular be gathered from FIGS. 6a and 6b, the bolt 142 is coupled by means of operating section 142a with a bolt auxiliary member 144 movable in translatory manner along axis 5, so that a translatory movement of said bolt auxiliary member 144 leads to a pivoting movement of bolt 142. For the force actuation of the bolt auxiliary member 144 are provided in not shown manner a permanent magnet 146 and an electromagnet 147, the permanent magnet 146 being constructed for force actuating the bolt auxiliary member 144 in the direction of arrow 5a, and the electromagnet 147 is constructed to force actuate the bolt auxiliary member 144 in the direction of arrow 5 on energization.

The engagement section 142b of bolt 142 serves to cooperate with the locking cam 175. In the locked state of the discharge device shown in FIGS. 6a and 6b, the engagement section 142 blocks a displacement of the push rod assembly 178 in the direction of arrow 6a to the left. Only when the bolt 142 has pivoted about rotation axis 4 in the direction of arrow 4a, is the blocking of the bolt component 178 eliminated, so that its release position can be reached. Bolt 142 is permanently moment-actuated in the direction of arrow 4a by the spring clip 148 shown in FIG. 7b and in the position of FIGS. 6a and 6b this is not sufficient for pivoting bolt 142, because it is held by the bolt auxiliary member 144 in its position shown in FIGS. 6a and 6c.

Operation will be explained in detail hereinafter relative to FIGS. 8a to 8c.

Figure 8A:
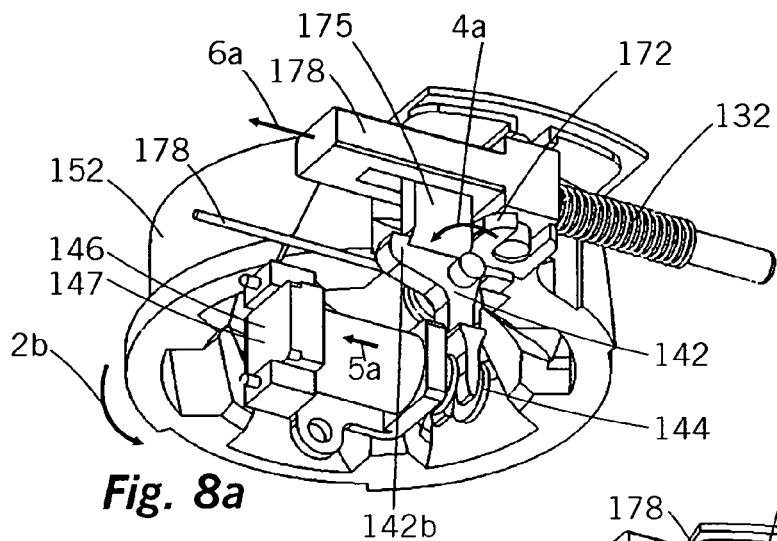
FIGS. 8a to 8c The locking mechanism of the embodiment of FIGS. 6a and 6b in different operating stages.

FIG. 8a shows the locked starting state of the discharge device, which is also shown in FIGS. 6a and 6b. As has already been explained, in this position of push rod component 178 a movement in direction 6a is impossible, because control cam 175 has a limited freedom of movement in direction 6a as a result of engagement section 142b. In this locked state 142, the bolt 142 is admittedly moment-actuated in direction of arrow 4a by spring 148, but said moment-actuation is not sufficient for rotating bolt 142, because in the represented state and in not shown manner the bolt auxiliary member 144 engages on permanent magnet 146 and the resulting holding moment on the bolt 142 exceeds the moment produced by spring 148.

In the locked state of FIG. 8a an operation of the discharge device is impossible for the reasons given in connection with the embodiment of FIGS. 1 to 5. On pressing down the operating member 188, the cams of the operating member 188 not shown in conjunction with this second embodiment would be prevented by the locking sections of locking member 152 from a displacement necessary for a discharge process.

Only on energizing electromagnet 147 through the not shown control electronics is it possible to bring about the release state of the discharge device. Energization of electromagnet 147 leads to a brief force actuation of the bolt auxiliary member 144 to the right in direction 5b. The force actuation by electromagnet 147 need not be very powerful, because it only needs together with the force actuation by the spring clip 148 on the bolt auxiliary member 144 to overcome the holding force in the opposite direction provided by permanent magnet 146. The displacement of the bolt auxiliary member 144 in direction 5b resulting from the energizing of electromagnet 147 leads as a result of the operative coupling of the bolt auxiliary member 144 with the bolt 142 simultaneously to a pivoting of bolt 142 in the direction of arrow 4a. As a result the engagement between engagement section 142b and locking cam 175 is ended, so that the push rod component 178 is displaced to the left in direction 6a until the locking cam strikes in not shown manner on the end of recess 114. The necessary energy for displacing the push rod component 178 comes from the release spring 132 which is only shown in FIG. 8a for simplification purposes.

Figure 8B:
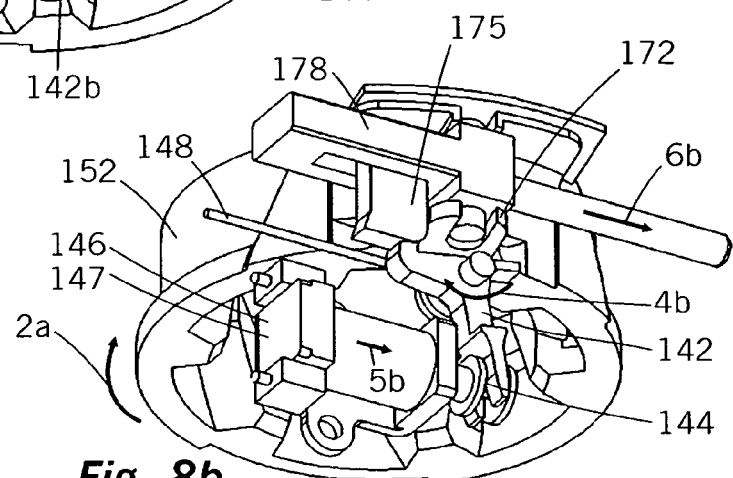
Figure 8C:
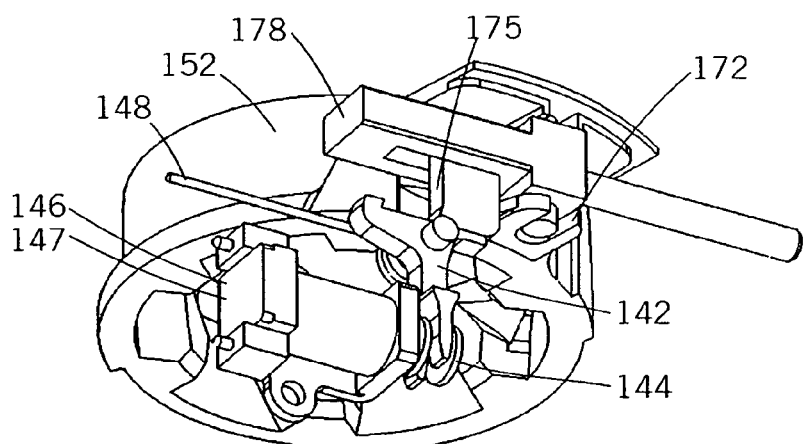

The state of FIG. 8b represents the resulting release state of the discharge device. Through the displacement of the push rod component 178 there has also been a rotation of locking member 152 in direction 2b, so that said locking member 152 is now in a position in which the cams of operating member 188 can be moved past the locking sections of locking member 152 so as to enable a discharge process. This corresponds to the state of FIGS. 3a to 3c of the first embodiment.

As has already been described relative to the first embodiment, the discharge process within the scope of the stroke and return stroke movements once again leads to a rotation of locking member 152 in the direction of arrow 2a. As a result of the forcible coupling of locking member 152 with push rod component 178 the latter is also moved in the direction of arrow 6b. In a first partial portion said movement initially has no consequences regarding the position of bolt 142. Only when locking cam 175 has come into the vicinity of the return section 142c of bolt 142, is the latter pivoted back in direction 4b counter to the tension of spring clip 148 until the bolt auxiliary member 144 again arrives in a position in which it is held by permanent magnet 146. The resulting state is shown in FIG. 8c. With regards to the locking member 152 and operating member 188 this state is comparable with that of FIGS. 5a to 5c.

In the same way as was described relative to the first embodiment, the movement of the locking member 152 in connection with the stroke and return stroke movements of the operating member 188 extends beyond the locked position of the push rod component 178 to the right in direction 6b and then, if the cams of the operating member 188 are disengaged from the locking sections of the locking member, there is then a movement of the push rod component 178 in the opposite direction 6a which brings said component 178 back into the locked position of FIGS. 6a, 6b and 8a. In this locked position the locking cam 175 again engages on the engagement section 142b of the bolt member 142, so that a discharge process is prevented until triggered again by the energizing of electromagnet 147.

Figure 9:
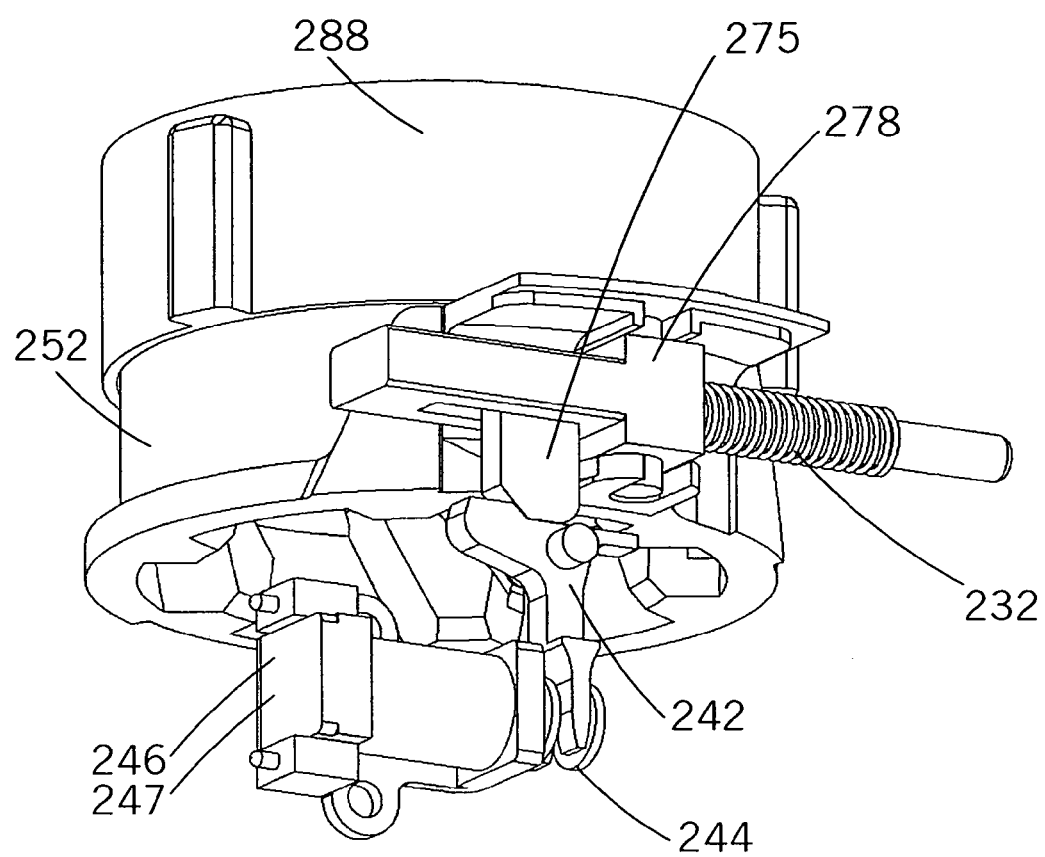
FIG. 9 A view of a part of a third embodiment of an inventive discharge device.

In a variant to said second embodiment shown in FIG. 9, there is no spring clip 148 which moment-actuates the bolt member 142 in direction 4a. Instead the moment-actuation of bolt member 142 takes place in the position where it no longer impedes the locking cam 275 and as a result of the latter and the release spring 232. To this end the contact area of the locking cam 275 is so shaped that the contact area in the locking position shown permanently moment-actuates the bolt member 242. In conjunction with the equidirectional moment-actuation by electromagnet 247, this leads to the overcoming of the force of permanent magnet 246 and to the pivoting of bolt member 242 as soon as the electromagnet 247 is energized.

Figure 10A:
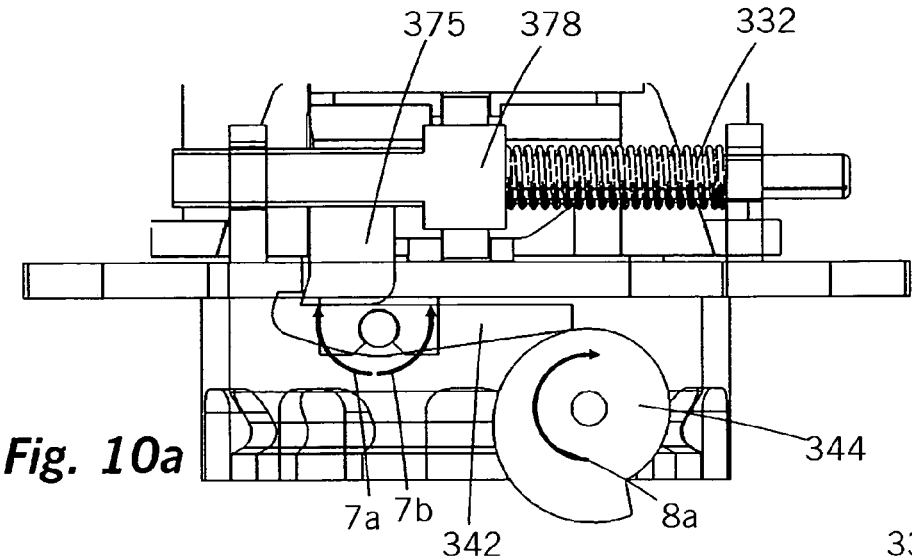
FIGS. 10a to 10c A side view of a fourth embodiment of an inventive discharge device.
Figure 10B:
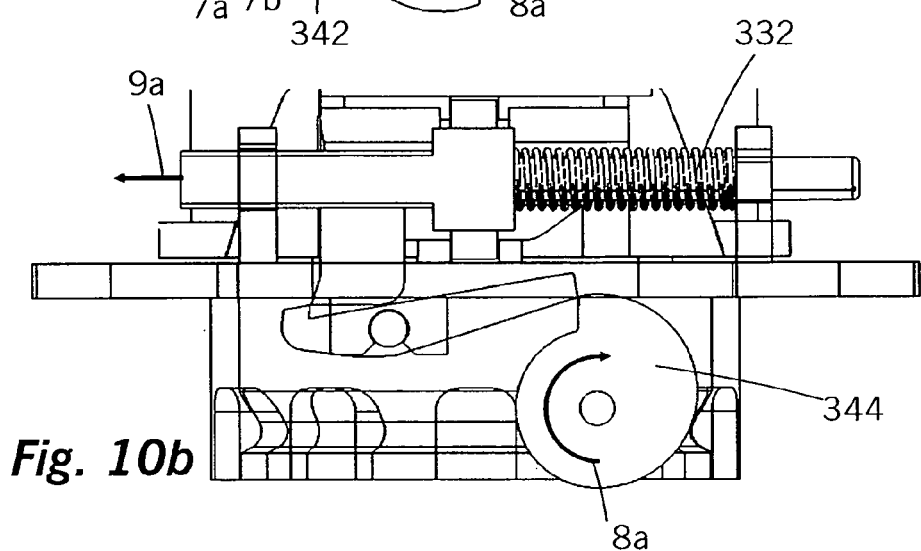
Figure 10C:
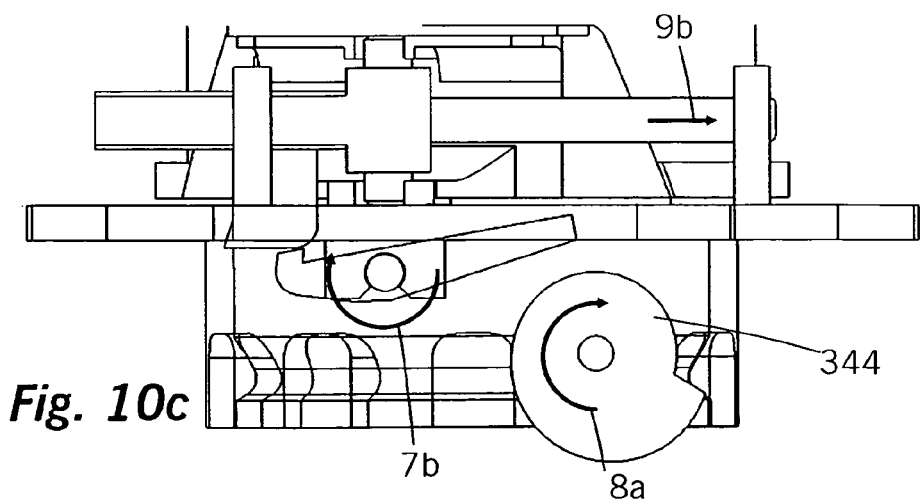

FIGS. 10a to 10c show a further embodiment of an inventive discharge device in side view. The difference compared with the second embodiment is that the bolt 342 is moment-actuated towards its blocking position, i.e. in the direction of arrow 7a, by a not shown spring and consequently blocks the locking cam 375 in the locked state of FIG. 10.

To release the locking cam 375, bolt 342 is pivoted by means of a cam disk 344. By rotating said cam disk 344 in the direction of arrow 8a the bolt 342 is pivoted in the direction of arrow 7b to such an extent that the locking cam 375 and therefore the push rod component 375 are disengaged and under the action of release spring 332 can be displaced to the right in direction 9a. The state immediately prior to disengagement is shown in FIG. 10b. As a result of the disengagement the release state shown in FIG. 10c is reached.

Following said disengagement the cam disk 344 is rotated on in direction of arrow 8a until again it reaches its basic position of FIG. 10a. As soon as a discharge operation again moves the push rod 378 to the right in direction 9b, starting from the release state of FIG. 10c, bolt 342 as a result of its spring moment actuation in direction 7a again engages with the locking cam 375, so that the locked state of FIG. 9a is obtained again.

Other than in the preceding embodiments, in this embodiment the disengagement and therefore the obtaining of the release state is not brought about by means of an electromagnet, but instead by a randomly designed motor provided for rotating cam disk 344. Such a motor can e.g. be an electric motor or preferably a piezoelectric motor. As in the preceding embodiments, said motor does not serve to make available the mechanical energy for moving the locking member 352 into its release or locked position, but merely to transfer the locking member 352 into its release position, so that the motor does not require a high power level.

FIGS. 11a to 12b show another embodiment of a discharge device according to the invention. In FIGS. 11a to 11c are illustrated partial views of the discharge device which are consistent with the embodiment of FIGS. 1 to 5 in relation to most of the components. The discharge device includes a locking mechanism 420 which may be consistent with the locking mechanism 20 shown in FIGS. 1 to 5. However, the locking mechanism 120 shown in FIGS. 6 to 8 or the locking mechanism shown in FIGS. 9 and 10 may be employed as well.

Also illustrated is a pump 414 including a pump chamber 415 and disposed inside of the housing of the discharge device. Said pump 414 is a piston pump, a piston 416 therein being manually displaceable in direction of arrow 1 to effect a volume variation of the pump chamber 415 together with the operating member 488, a nose olive 482, and an operating handle (not illustrated). A specific feature of said pump is the design of an inlet valve 417. Said inlet valve 417 includes on a valve body 418 a circumferential valve lip 418a pointing to the inside and provided at the lower end of the valve body 418, and corresponding thereto a pump chamber fixed inlet port 417a, with the outer circumference thereof being adapted to the inner circumference of the valve lip 418a.

The operation principle of said pump 414 is as follows: during a stroke movement of the operating member 488 in a direction 1a, the piston 415 and the valve body 418 are moved at first. As soon as the valve lip 418a will contact the inlet port 417a and be pushed upon said port, the pump chamber 415 is sealed in direction of an inlet duct 414a. A further movement of the piston 416 will then result in a pressure controlled displacement of the valve body 418 in the direction 1a, said movement occurring faster than the displacement of piston 416 in the same direction. As a consequence, a pump outlet valve 419 opens which is composed by a tapered tip 418b of the valve body 418 and an outlet duct 416a in the piston 416. The discharge operation starts. As subsequently there is no manual application of force by the operating member 488, the piston 416 and the valve body 418 are displaced by the pump spring in a return stroke direction 1b, what initially will not effect a refilling of the pump chamber 415, as the valve lip 418a abuts on the inlet port 417a for a predominant portion of the return stroke path. Instead, a vacuum is produced in the pump chamber 415. Not until the valve lip 418a will disengage from the inlet port 417a and thus open the inlet valve 417, said vacuum results in an abrupt aspiration of medium through the inlet duct 414a. Such a separation of valve lip 418a and inlet port 417a will occur near the end of the return stroke, as soon as the operating member 488 and the locking member 452 disengage.

Figure 12A:
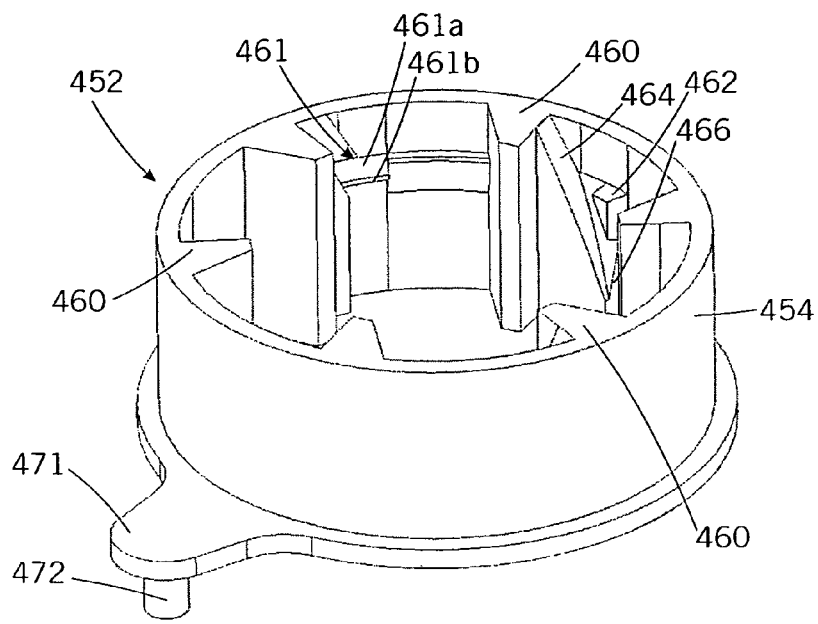
FIGS. 12a and 12b The locking member of the embodiment of FIGS. 11a to 11c.
Figure 12B:
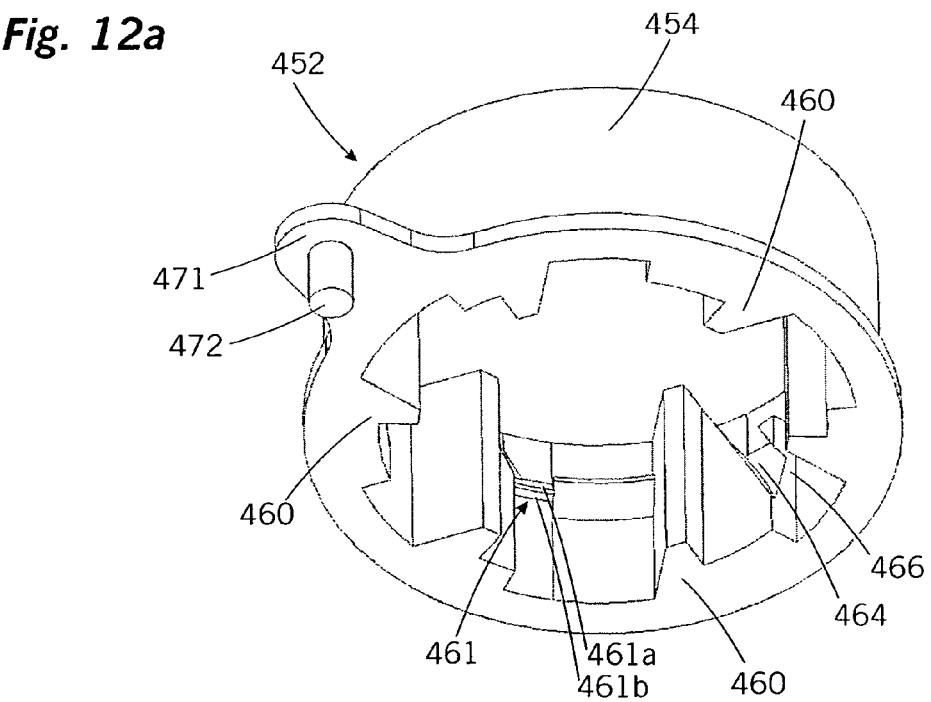

The use of such a pump 414, which does not refill the pump chamber 415 over a substantial portion of the return stroke and will perform said refilling only upon reaching an intermediate filling position of the piston, becomes obvious in combination with the illustrations of FIGS. 12a and 12b. Said figures show in different views the locking ring 452 of the discharge device according to FIG. 11a. Said locking ring 452 is corresponding to the locking ring illustrated in FIGS. 1e and 1f, regarding most of the features. It has a lateral wall 454 with a radially outwards extending protrusion 471, to which a guide pin 472 is provided, which is consistent to the guide fork 72 of the embodiment shown in FIGS. 1e and 1f in relation to its function. In contrast to the configuration of FIGS. 1e and 1f, there is not a total of six functional sections, but instead there are only three functional sections 460 having connecting link grooves 464, 466 formed at the inside of the lateral wall 454. Between each of said three functional sections 460 are respective locking steps 461 disposed which have a chamfer 461a at the upturned surface thereof, and which have an essentially radially directed locking edge 461b at the bottom side.

The action of said locking steps 461 is as follows: If the operating member 488 is pressed downwards from a non-locked starting position according to FIG. 11a in the direction of arrow 1a, said operation results first in a turning of the locking ring 452 in a manner as described in the above embodiments, and simultaneously a medium discharge is started. As soon as the cams 494 of the operating member 488 reach the vicinity of the locking steps 461, they are deflected radially inwards by the chamfers 461a and go back to a non-deflected condition after overriding the locking steps 461 in the vicinity of the locking edges 461b. After reaching said condition, a return of the operating member 488 to the previously occupied starting position is inhibited for the time being, as the cams 94 can not be lead across the return steps 461 in the return stroke direction 1b, as shown in FIG. 11b. As a consequence, the only way to retransfer the operating member 488 to its non-operated starting position, is to complete the started stroke movement in the direction 1a, and thus to effect a return of the cams 494 along the second connecting link groove sections 466 in the above described manner. Indeed, said procedure mandatorily results in a rearrangement of the locking condition in the above described manner.

The configuration which after reaching the intermediate position of FIG. 11b allows a return to the starting position of FIG. 11a only by passing through the end position according to FIG. 11c, prevents in connection with the above described design of the pump 414 that a user may misuse the discharge device by executing repeated partial stroke movements, wherein the cams 494 are reciprocated between the locking edge 461b and the bottom edge 452a of the locking member 452. Such an operation will not be successful, for due to the design of the inlet valve 417 of the pump 414, a refilling of the pump chamber 415 is not feasible. As mentioned above, the pump chamber 415 is not refilled until the return stroke movement in the direction 1b is almost completed or has been completed. A movement of the operating member 488 in the direction 1b to make the cams 494 abut the locking edges 461b, is not sufficient to that end. As soon as the cams are moved along the second connecting link groove sections 466 in the direction 1b in relation to the locking member 452, said refilling of the pump chamber 415 is achieved. Indeed, as said procedure will mandatorily also reconstruct the locking condition, any misuse is inhibited.

In a not illustrated variant of the embodiment of FIGS. 11a to 12b, a plurality of steps are provided in succession along the stroke movement 1a, instead of only one corresponding locking step 461 per cam 494, so that a return stroke is almost completely prevented as in the course of the stroke movement, after an overriding in the stroke direction 1a, said locking steps forming a ladder-type detent device prevent any retraction in the return stroke direction 1b.

The invention claimed is:

1. A discharge device for media comprising:
    a housing;
    an operating member manually movable relative to the housing and which for operating a discharge mechanism can be transferred from an unoperated starting position in an operating direction into an operated end position;
    a locking member displaceable between a locked position in which the locking member prevents displacement of the operating member into the end position and a release position in which the locking member allows the displacement of the operating member into the end position with respect to the housing; and
    a first spring which applies a force to the locking member in a direction of the release position of the locking member;
    the operating member and the locking member being so operatively coupled together in the release position such that at least one of a stroke movement of the operating member from the unoperated starting position into the operated end position and a following return stroke movement from the operated end position into the starting position is brought about by transmission mechanism bringing about a supply of energy into the first spring.

2. The discharge device according to claim 1, wherein the operating member and the locking member are coupled together by a connecting link guide, by which the stroke movement or the following return stroke movement of the operating member brings about the displacement of the locking member.

3. The discharge device according to claim 2, wherein the connecting link guide has at least one connecting link groove on the locking member and at least one cam for engagement in the connecting link groove on the operating member, the connecting link guide being constructed in such a way that the connecting link guide has a first connecting link groove section into which is introduced the cam during the stroke movement or a second connecting link groove section into which the cam can be introduced towards an end of the stroke movement or on passing into the following return stroke movement.

4. The discharge device according to claim 1, wherein the stroke movement of the operating member in the locked position of the locking member is at least sectorwise prevented in that at least one locking member-side locking section blocks a stroke movement path of the at least one operating member-side locking section.

5. The discharge device according to claim 1, wherein an electric motor or piezoelectric motor is provided for moving the locking member, a locking auxiliary member, a bolt member or a bolt auxiliary member.

6. The discharge device according to claim 5, wherein the motor is provided for movement of a cam member, the cam member being constructed for
directly preventing movement of the locking member or a locking auxiliary member in the locked position of the locking member, or
indirectly via a bolt member, to prevent movement of the locking member or the locking auxiliary member in the locked position of the locking member.

7. A discharge device for media comprising:
a housing;
an operating member manually movable relative to the housing and which for operating a discharge mechanism can be transferred from an unoperated starting position in an operating direction into an operated end position;
a locking member displaceable between a locked position in which the locking member prevents displacement of the operating member into the end position and a release position in which the locking member allows the displacement of the operating member into the end position, with respect to the housing; and
a control arrangement constructed so as to block movement of the locking member relative to the housing in a blocking state and
through a triggering action attainable by an electric signal allows the displacement of the locking member from the locked position into the release position.

8. The discharge device according to claim 7, wherein the control arrangement is constructed in such a way that on displacement of the locking member into the locked position, the control arrangement is automatically transferred into a blocking state.

9. The discharge device according to claim 7, wherein a bolt member is provided, which in a blocking state of the control arrangement mechanically blocks the displacement of the locking member or a locking auxiliary member operatively connected to the locking member.

10. The discharge device according to claim 7, wherein, in a blocking state of the control arrangement,
the locking member or a locking auxiliary member operatively connected to the locking member is held by a permanent magnet in a position leading to the locking member being placed in the locked position of the locking member, or
a bolt member or a bolt auxiliary member operatively connected to the bolt member is held by the permanent magnet in a position leading to mechanical blocking of the locking member by the bolt member.

11. The discharge device according to claim 10, wherein a force exerted by the permanent magnet in the locked position of the locking member on the locking member, the locking auxiliary member, the bolt member, or the bolt auxiliary member is higher than a force applied by a spring of the discharge device in the locked position of the locking member and in an opposite direction on the locking member, the locking auxiliary member, the bolt member, or the bolt auxiliary member.

12. The discharge device according to claim 7, further including an electrically controllable actuator for bringing about the triggering action through which
the locking member or a locking auxiliary member operatively connected to the locking member can be force-actuated, so that the locking member is displaced in a direction of the release position or
a bolt member or a bolt auxiliary member operatively connected to the bolt member is force-actuated in a direction leading to an elimination of mechanical blocking of the locking member by the bolt member and therefore to a displacement of the locking member towards the release position.

13. A discharge device according to claim 12, wherein the electrically controllable actuator is constructed for exerting a force on the locking member, the locking auxiliary member, the bolt member, or the bolt auxiliary member, which is higher than a force in an opposite direction resulting from a force of a permanent magnet on the corresponding member.

14. A discharge device for media comprising:
a housing;
an operating member manually movable relative to the housing and which for operating a discharge mechanism can be transferred from an unoperated starting position in an operating direction into an operated end position; and
a locking member displaceable between a locked position in which the locking member prevents displacement of the operating member into the end position and a release position in which the locking member allows the displacement of the operating member into the end position with respect to the housing;
wherein, for transfer from the locked position into the release position, the locking member is constructed to rotate about a rotation axis oriented in the operating direction and has distributed over a circumference of the locking member at least three locking sections, which are so positioned in the locked position of the locking member that a stroke movement of the operating member is prevented.

15. The discharge device according to claim 14, wherein the locking member surrounds in all-round manner the operating member and a rotation axis of the locking member is oriented parallel to the operating direction.

16. The discharge device according to claim 14, wherein the locking sections of the locking member facing the locking member point radially inward from an inner face of the locking member and the locking sections of the locking member facing the operating member point radially outward.

17. A discharge device for media comprising:
a housing;
an operating member manually movable relative to the housing and which for operating a discharge mechanism can be transferred from an unoperated starting position in an operating direction into an operated end position;
a locking member displaceable between a locked position in which the locking member prevents displacement of the operating member into the end position and a release position in which the locking member allows the displacement of the operating member into the end position, with respect to the housing; and a return lock, which after reaching a defined intermediate locking position during a transition of the operating member from the starting position in a direction of the end position, prevents a return of the operating member to the starting position as long as the operating member will be transferred to the end position.

18. The discharge device according to claim 17, wherein the discharge mechanism is a pump having a volume variable pump chamber, the pump being configured in such a way that a filling of the pump chamber within a return stroke will not occur until a defined intermediate filling position is reached, the intermediate filling position being arranged in such a way that the intermediate filling position will be reached when the operating member is positioned at a location between the intermediate locking position and the starting position.

19. The discharge device according to claim 17, wherein the return lock has a detent, a first component of the detent being disposed fixedly relative to the housing in an operating direction and a second component of the detent, which is constructed for cooperation with the first component, being disposed fixedly relative to the operating member in the operating direction.

* * * * *